(12) United States Patent
Hansen et al.

(10) Patent No.: US 11,039,734 B2
(45) Date of Patent: Jun. 22, 2021

(54) REAL TIME CORRELATED DEPICTION SYSTEM OF SURGICAL TOOL

(71) Applicant: 3DIntegrated Aps, København N. (DK)

(72) Inventors: Steen Møller Hansen, Skødstrup (DK); Henriette Schultz Kirkegaard, Copenhagen V (DK)

(73) Assignee: 3DIntegrated Aps, København N. (DK)

( * ) Notice: Subject to any disclaimer, the term of this patent is extended or adjusted under 35 U.S.C. 154(b) by 205 days.

(21) Appl. No.: 15/601,276

(22) Filed: May 22, 2017

(65) Prior Publication Data

US 2017/0251900 A1 Sep. 7, 2017

Related U.S. Application Data

(63) Continuation of application No. PCT/DK2016/050180, filed on Jun. 13, 2016.

(51) Int. Cl.
*H04N 13/00* (2018.01)
*A61B 1/00* (2006.01)
(Continued)

(52) U.S. Cl.
CPC ........ *A61B 1/0005* (2013.01); *A61B 1/00193* (2013.01); *A61B 1/04* (2013.01);
(Continued)

(58) Field of Classification Search
CPC ..... A61B 1/0005; A61B 1/3132; A61B 90/37; A61B 1/00193; A61B 1/04; G06T 19/20; G06T 15/08; G01B 11/24
See application file for complete search history.

(56) References Cited

U.S. PATENT DOCUMENTS 3,919,541 A 11/1975 Chao
4,694,434 A 9/1987 von Ramm et al.
(Continued)

FOREIGN PATENT DOCUMENTS

CA 2 603 353 A1 9/2007
CN 2533818 Y 2/2003
(Continued)

OTHER PUBLICATIONS

European Patent Application No. 16853132.5, by 3dintegrated ApS: Supplementary European Search Report, dated Oct. 27, 2017 (4 pages).
(Continued)

*Primary Examiner* — Richard T Torrente
(74) *Attorney, Agent, or Firm* — Mintz Levin Cohn Ferris Glovsky and Popeo, P.C.

(57) ABSTRACT

A depiction system for generating a real time correlated depiction of movements of a surgical tool for uses in minimally invasive surgery is described. In an embodiment the system includes a computer system, 3D surface data generation means and position data generation means for obtaining real time spatial position data of at least a part of the surgical tool. The 3D surface data generation means or the position data generation is adapted for providing surface position data of at least the target area. The computer system is programmed for determining depiction data representing a depiction of the real time relative spatial position(s) of the surgical tool onto at least a portion of the surface contour of the surface section of the minimally invasive surgery cavity.

38 Claims, 21 Drawing Sheets

(51) Int. Cl.
*A61B 1/04* (2006.01)
*G01B 11/24* (2006.01)
*A61B 90/00* (2016.01)
*A61B 1/313* (2006.01)
*G06T 15/08* (2011.01)
*G06T 19/20* (2011.01)

(52) U.S. Cl.
CPC ............ *A61B 1/3132* (2013.01); *A61B 90/37* (2016.02); *G01B 11/24* (2013.01); *G06T 15/08* (2013.01); *G06T 19/20* (2013.01)

(56) References Cited

U.S. PATENT DOCUMENTS

| | | | |
|---|---|---|---|
| 4,877,016 A | 10/1989 | Kantor et al. | |
| 4,887,222 A | 12/1989 | Miyake et al. | |
| 5,457,439 A * | 10/1995 | Kuhn | B60K 35/00 340/435 |
| 5,588,949 A | 12/1996 | Taylor et al. | |
| 5,651,783 A | 7/1997 | Reynard | |
| 5,710,870 A | 1/1998 | Ohm et al. | |
| 5,725,523 A | 3/1998 | Mueller | |
| 5,747,953 A | 5/1998 | Philipp | |
| 5,754,717 A | 5/1998 | Esch | |
| 5,769,791 A | 6/1998 | Benaron et al. | |
| 5,836,869 A | 11/1998 | Kudo et al. | |
| 5,888,194 A | 3/1999 | Utsumi et al. | |
| 5,933,223 A | 8/1999 | Flock et al. | |
| 5,951,142 A | 9/1999 | Wang et al. | |
| 5,976,077 A | 11/1999 | Wittens et al. | |
| 5,989,181 A | 11/1999 | Duetting et al. | |
| 6,006,127 A | 12/1999 | Van Der Brug et al. | |
| 6,017,354 A | 1/2000 | Culp et al. | |
| 6,036,636 A | 3/2000 | Motoki et al. | |
| 6,165,184 A | 12/2000 | Verdura et al. | |
| 6,361,530 B1 | 3/2002 | Mersch | |
| 6,387,044 B1 | 5/2002 | Tachibana et al. | |
| 6,471,638 B1 | 10/2002 | Chang et al. | |
| 6,494,827 B1 | 12/2002 | Matsumoto et al. | |
| 6,522,806 B1 | 2/2003 | James, IV et al. | |
| 6,527,704 B1 | 3/2003 | Chang et al. | |
| 6,537,290 B2 | 3/2003 | Adams et al. | |
| 6,549,288 B1 | 4/2003 | Migdal et al. | |
| 6,631,271 B1 | 10/2003 | Logan | |
| 6,659,943 B2 | 12/2003 | Watanabe et al. | |
| 6,741,883 B2 | 5/2004 | Gildenberg | |
| 6,791,601 B1 | 9/2004 | Chang et al. | |
| 6,810,184 B2 | 10/2004 | Skutnik | |
| 6,811,546 B1 | 11/2004 | Callas et al. | |
| 6,908,428 B2 | 6/2005 | Aizenfeld et al. | |
| 6,945,981 B2 | 9/2005 | Donofrio et al. | |
| 7,037,314 B2 | 5/2006 | Armstrong | |
| 7,049,594 B2 | 5/2006 | Wu et al. | |
| 7,063,695 B2 | 6/2006 | Nield et al. | |
| 7,113,675 B2 | 9/2006 | Nield et al. | |
| 7,211,044 B2 | 5/2007 | Mast et al. | |
| 7,422,327 B2 | 9/2008 | Smith | |
| 7,464,846 B2 | 12/2008 | Shelton, IV et al. | |
| 7,505,808 B2 | 3/2009 | Anderson et al. | |
| 7,725,214 B2 | 5/2010 | Diolaiti | |
| 7,775,969 B2 | 8/2010 | Teichmann | |
| 7,784,947 B2 | 8/2010 | Perez et al. | |
| 7,843,558 B2 | 11/2010 | Furman | |
| 7,845,537 B2 | 12/2010 | Shelton, IV et al. | |
| 7,876,942 B2 | 1/2011 | Gilboa | |
| 7,912,532 B2 | 3/2011 | Schmidt et al. | |
| 7,927,272 B2 | 4/2011 | Bayer et al. | |
| 7,976,459 B2 | 7/2011 | Laser | |
| 8,064,819 B2 | 11/2011 | Ingrassia et al. | |
| 8,086,008 B2 | 12/2011 | Coste-Maniere et al. | |
| 8,162,826 B2 | 4/2012 | Pecherer et al. | |
| 8,165,351 B2 | 4/2012 | Bendall | |
| 8,182,422 B2 | 5/2012 | Bayer et al. | |
| 8,211,044 B2 | 7/2012 | Liebowitz | |
| 8,242,390 B2 | 8/2012 | Prest et al. | |
| 8,242,398 B2 | 8/2012 | Young et al. | |
| 8,340,379 B2 | 12/2012 | Razzaque et al. | |
| 8,397,335 B2 | 3/2013 | Gordin et al. | |
| 8,403,843 B2 | 3/2013 | Bruto Da Costa | |
| 8,409,076 B2 | 4/2013 | Pang et al. | |
| 8,443,007 B1 | 5/2013 | Kindig et al. | |
| 8,480,566 B2 | 7/2013 | Farr | |
| 8,512,368 B2 | 8/2013 | Sato et al. | |
| 8,525,059 B2 | 9/2013 | Berger et al. | |
| 8,527,033 B1 | 9/2013 | Williams et al. | |
| 8,531,511 B2 | 9/2013 | Katakura | |
| 8,554,307 B2 | 10/2013 | Razzaque et al. | |
| 8,568,304 B2 | 10/2013 | Vayser et al. | |
| 8,632,535 B2 | 1/2014 | Shelton, IV et al. | |
| 8,657,809 B2 | 2/2014 | Schoepp | |
| 8,670,816 B2 | 3/2014 | Green et al. | |
| 8,672,207 B2 | 3/2014 | Shelton, IV et al. | |
| 8,708,211 B2 | 4/2014 | Zemlok et al. | |
| 8,721,525 B2 | 5/2014 | Heckele et al. | |
| 8,750,568 B2 | 6/2014 | Frank et al. | |
| 8,780,362 B2 | 7/2014 | Sharonov et al. | |
| 8,880,151 B1 | 11/2014 | Stolka et al. | |
| 8,892,191 B2 | 11/2014 | Brennan et al. | |
| 8,922,781 B2 | 12/2014 | Tearney et al. | |
| 8,968,347 B2 | 3/2015 | McCollam | |
| 8,988,505 B2 | 3/2015 | Schaerer et al. | |
| 9,008,757 B2 | 4/2015 | Wu | |
| 9,179,984 B2 | 11/2015 | Teichman et al. | |
| 2001/0025174 A1 | 9/2001 | Daniel et al. | |
| 2001/0027272 A1* | 10/2001 | Saito | A61B 34/20 600/426 |
| 2001/0040990 A1 | 11/2001 | Dadi | |
| 2001/0055462 A1 | 12/2001 | Seibel | |
| 2002/0028986 A1 | 3/2002 | Thompson | |
| 2002/0049435 A1 | 4/2002 | Mersch | |
| 2002/0049464 A1 | 4/2002 | Donofrio et al. | |
| 2002/0087179 A1 | 7/2002 | Culp et al. | |
| 2002/0123665 A1 | 9/2002 | Miller | |
| 2002/0137987 A1 | 9/2002 | Watanabe et al. | |
| 2003/0013960 A1 | 1/2003 | Makin et al. | |
| 2003/0029464 A1 | 2/2003 | Chen et al. | |
| 2003/0095781 A1 | 5/2003 | Williams | |
| 2003/0118302 A1 | 6/2003 | James, IV et al. | |
| 2004/0022527 A1 | 2/2004 | Carusillo et al. | |
| 2004/0064019 A1 | 4/2004 | Chang et al. | |
| 2004/0122292 A1 | 6/2004 | Dey et al. | |
| 2004/0145746 A1 | 7/2004 | Kim et al. | |
| 2004/0188616 A1 | 9/2004 | Wu et al. | |
| 2005/0004592 A1 | 1/2005 | Criscuolo | |
| 2005/0005024 A1 | 1/2005 | Samuels et al. | |
| 2005/0054894 A1 | 3/2005 | Aizenfeld et al. | |
| 2005/0085718 A1 | 4/2005 | Shahidi | |
| 2005/0131476 A1 | 6/2005 | Moctezuma de la Barrera et al. | |
| 2005/0135749 A1 | 6/2005 | Nield et al. | |
| 2006/0004406 A1 | 1/2006 | Wehrstein et al. | |
| 2006/0036162 A1 | 2/2006 | Shahidi et al. | |
| 2006/0069314 A1 | 3/2006 | Farr | |
| 2006/0114473 A1 | 6/2006 | Tearney et al. | |
| 2006/0171693 A1 | 8/2006 | Todd et al. | |
| 2006/0235270 A1 | 10/2006 | Teichmann | |
| 2006/0235279 A1 | 10/2006 | Hawkes et al. | |
| 2006/0241347 A1 | 10/2006 | Whitehead | |
| 2006/0258938 A1 | 11/2006 | Hoffman et al. | |
| 2007/0060098 A1 | 3/2007 | McCoy | |
| 2007/0112336 A1 | 5/2007 | Aizenfeld et al. | |
| 2007/0112337 A1 | 5/2007 | Salman et al. | |
| 2007/0147707 A1 | 6/2007 | Coste-Maniere et al. | |
| 2007/0151390 A1 | 7/2007 | Blumenkranz et al. | |
| 2007/0167679 A1 | 7/2007 | Miyamoto et al. | |
| 2007/0175964 A1 | 8/2007 | Shelton, IV et al. | |
| 2007/0179488 A1 | 8/2007 | Trusty et al. | |
| 2007/0206275 A1 | 9/2007 | Hemmer et al. | |
| 2007/0225550 A1 | 9/2007 | Gattani et al. | |
| 2007/0250006 A1 | 10/2007 | Court et al. | |
| 2007/0255101 A1 | 11/2007 | Bar-Or | |
| 2007/0260121 A1 | 11/2007 | Bakos et al. | |
| 2008/0009677 A1 | 1/2008 | Shoroji et al. | |
| 2008/0058989 A1 | 3/2008 | Oleynikov et al. | |
| 2008/0071140 A1 | 3/2008 | Gattani et al. | |

(56) References Cited

U.S. PATENT DOCUMENTS

| | | |
|---|---|---|
| 2008/0159653 A1 | 7/2008 | Dunki-Jacobs et al. |
| 2008/0167522 A1 | 7/2008 | Giordano et al. |
| 2008/0167671 A1 | 7/2008 | Giordano et al. |
| 2008/0188716 A1 | 8/2008 | Heckele et al. |
| 2008/0208006 A1 | 8/2008 | Farr |
| 2008/0208041 A1 | 8/2008 | Gilboa |
| 2008/0319311 A1 | 12/2008 | Hamadeh |
| 2009/0017430 A1 | 1/2009 | Muller-Daniels et al. |
| 2009/0054767 A1 | 2/2009 | Telischak et al. |
| 2009/0192519 A1 | 7/2009 | Omori |
| 2009/0203991 A1 | 8/2009 | Papaioannou et al. |
| 2009/0209998 A1 | 8/2009 | Widmann |
| 2009/0218527 A1 | 9/2009 | French et al. |
| 2009/0225320 A1* | 9/2009 | Bendall .............. G01B 11/25 356/447 |
| 2009/0240111 A1 | 9/2009 | Kessler et al. |
| 2009/0244260 A1 | 10/2009 | Takahashi et al. |
| 2009/0248041 A1 | 10/2009 | Williams et al. |
| 2009/0270682 A1 | 10/2009 | Visser |
| 2009/0318756 A1 | 12/2009 | Fisher et al. |
| 2009/0318758 A1 | 12/2009 | Farr et al. |
| 2009/0318763 A1 | 12/2009 | Koerner et al. |
| 2009/0323053 A1 | 12/2009 | Furman |
| 2010/0036393 A1 | 2/2010 | Unsworth |
| 2010/0065605 A1 | 3/2010 | Shelton, VI et al. |
| 2010/0065609 A1 | 3/2010 | Schwemberger |
| 2010/0069920 A1 | 3/2010 | Naylor et al. |
| 2010/0096435 A1 | 4/2010 | Fuchs et al. |
| 2010/0106015 A1 | 4/2010 | Norris |
| 2010/0200636 A1 | 8/2010 | Zemlok et al. |
| 2010/0228092 A1 | 9/2010 | Ortiz et al. |
| 2010/0268067 A1 | 10/2010 | Razzaque et al. |
| 2011/0069159 A1 | 3/2011 | Soler et al. |
| 2011/0110114 A1 | 5/2011 | Papac et al. |
| 2011/0112377 A1 | 5/2011 | Papac et al. |
| 2011/0161054 A1* | 6/2011 | Woolf .............. G06F 17/00 703/1 |
| 2011/0165535 A1 | 7/2011 | Berger et al. |
| 2011/0208004 A1 | 8/2011 | Feingold et al. |
| 2011/0237915 A1 | 9/2011 | Yamaguchi |
| 2011/0275901 A1 | 11/2011 | Shelton, IV |
| 2011/0282160 A1 | 11/2011 | Bhadri et al. |
| 2012/0024934 A1 | 2/2012 | Shelton, IV et al. |
| 2012/0062724 A1 | 3/2012 | Yokota |
| 2012/0071711 A1 | 3/2012 | Shelton, IV et al. |
| 2012/0071757 A1 | 3/2012 | Salcudean et al. |
| 2012/0082970 A1 | 4/2012 | Pravong et al. |
| 2012/0101497 A1 | 4/2012 | Jayaraj |
| 2012/0108901 A1 | 5/2012 | Sargeant et al. |
| 2012/0116369 A1 | 5/2012 | Viola |
| 2012/0130162 A1 | 5/2012 | Dolt et al. |
| 2012/0143049 A1 | 6/2012 | Neubauer et al. |
| 2012/0184951 A1 | 7/2012 | Viola |
| 2012/0209123 A1 | 8/2012 | King |
| 2012/0238808 A1 | 9/2012 | Teichtmann |
| 2012/0265009 A1 | 10/2012 | Yang et al. |
| 2012/0265010 A1 | 10/2012 | Uram |
| 2012/0265071 A1 | 10/2012 | Berke |
| 2012/0296163 A1 | 11/2012 | Stopek |
| 2012/0302828 A1 | 11/2012 | Toledo-Crow et al. |
| 2013/0038836 A1 | 2/2013 | Smith |
| 2013/0053782 A1 | 2/2013 | Shelton, IV |
| 2013/0053835 A1 | 2/2013 | Bacher et al. |
| 2013/0060084 A1 | 3/2013 | Fouts et al. |
| 2013/0070070 A1 | 3/2013 | Katakura |
| 2013/0103023 A1 | 4/2013 | Monson et al. |
| 2013/0110005 A1 | 5/2013 | Sharonov |
| 2013/0110006 A1 | 5/2013 | Sharonov et al. |
| 2013/0110129 A1 | 5/2013 | Reid et al. |
| 2013/0123800 A1 | 5/2013 | Leroy et al. |
| 2013/0144267 A1 | 6/2013 | Chan et al. |
| 2013/0226037 A1 | 6/2013 | Pinto et al. |
| 2013/0190759 A1 | 7/2013 | Waaler et al. |
| 2013/0197317 A1 | 8/2013 | Daniel et al. |
| 2013/0218024 A1 | 8/2013 | Boctor et al. |
| 2013/0226156 A1 | 8/2013 | Sharonov |
| 2013/0267787 A1 | 10/2013 | Warnock |
| 2013/0267975 A1 | 10/2013 | Timm et al. |
| 2013/0281845 A1 | 10/2013 | Luken |
| 2013/0296712 A1 | 11/2013 | Durvasula |
| 2013/0317351 A1 | 11/2013 | Case et al. |
| 2013/0317352 A1 | 11/2013 | Case et al. |
| 2013/0317353 A1 | 11/2013 | Frank et al. |
| 2013/0324999 A1 | 12/2013 | Price et al. |
| 2013/0345513 A1 | 12/2013 | Tsuruta et al. |
| 2014/0005484 A1 | 1/2014 | Charles |
| 2014/0005682 A1 | 1/2014 | Worrell et al. |
| 2014/0012078 A1 | 1/2014 | Coussa |
| 2014/0012286 A1 | 1/2014 | Lee et al. |
| 2014/0025067 A1 | 1/2014 | Kerr et al. |
| 2014/0030669 A1 | 1/2014 | Hey et al. |
| 2014/0031665 A1 | 1/2014 | Pinto et al. |
| 2014/0051994 A1 | 2/2014 | Graumann et al. |
| 2014/0052005 A1 | 2/2014 | Yokota |
| 2014/0066784 A1 | 3/2014 | Yokota |
| 2014/0071239 A1 | 3/2014 | Yokota |
| 2014/0071257 A1 | 3/2014 | Yokota |
| 2014/0074116 A1 | 3/2014 | Collins |
| 2014/0088410 A1 | 3/2014 | Wu |
| 2014/0106626 A1 | 4/2014 | Frushour et al. |
| 2014/0107417 A1 | 4/2014 | McKinley et al. |
| 2014/0107471 A1* | 4/2014 | Haider .............. A61B 1/3132 600/424 |
| 2014/0107685 A1 | 4/2014 | O'Neill et al. |
| 2014/0114327 A1 | 4/2014 | Boudreaux et al. |
| 2014/0121507 A1 | 5/2014 | Nau, Jr. |
| 2014/0121508 A1 | 5/2014 | Latimer et al. |
| 2014/0148799 A1 | 5/2014 | Mueller |
| 2014/0163359 A1 | 6/2014 | Sholev et al. |
| 2014/0171962 A1 | 6/2014 | Kang |
| 2014/0180001 A1 | 6/2014 | Von Grunberg et al. |
| 2014/0194896 A1 | 7/2014 | Frimer et al. |
| 2014/0200406 A1 | 7/2014 | Bennett et al. |
| 2014/0200561 A1 | 7/2014 | Ingmanson et al. |
| 2014/0204702 A1 | 7/2014 | Ratering |
| 2014/0207002 A1 | 7/2014 | Seow |
| 2014/0235946 A1 | 8/2014 | Smith |
| 2014/0236177 A1 | 8/2014 | Verner et al. |
| 2014/0243658 A1 | 8/2014 | Breisacher et al. |
| 2014/0275764 A1 | 9/2014 | Shen et al. |
| 2014/0275771 A1 | 9/2014 | Henley et al. |
| 2014/0276097 A1 | 9/2014 | Sharonov |
| 2014/0296636 A1 | 10/2014 | Hatano |
| 2014/0303491 A1 | 10/2014 | Shekhar et al. |
| 2014/0357945 A1 | 12/2014 | Duckworth |
| 2014/0367444 A1 | 12/2014 | Williams |
| 2014/0367591 A1 | 12/2014 | Mahou et al. |
| 2015/0005748 A1 | 1/2015 | Sniffin et al. |
| 2015/0018622 A1 | 1/2015 | Tesar et al. |
| 2015/0049907 A1 | 2/2015 | Hong et al. |
| 2015/0065875 A1 | 3/2015 | Friebe |
| 2015/0069108 A1 | 3/2015 | Williams |
| 2015/0073398 A1 | 3/2015 | Toledo-Crow et al. |
| 2015/0076211 A1 | 3/2015 | Irka et al. |
| 2015/0080660 A1 | 3/2015 | Gomez et al. |
| 2015/0080764 A1 | 3/2015 | Poe |
| 2015/0086162 A1 | 3/2015 | Miyahara et al. |
| 2015/0088115 A1 | 3/2015 | Smith |
| 2015/0109427 A1 | 4/2015 | Wood et al. |
| 2015/0119637 A1 | 4/2015 | Alvarez et al. |
| 2015/0133960 A1 | 5/2015 | Lohmeier et al. |
| 2015/0173591 A1 | 6/2015 | Zheng et al. |
| 2015/0230866 A1 | 8/2015 | Tung et al. |
| 2015/0238276 A1 | 8/2015 | Atarot et al. |
| 2015/0265792 A1 | 9/2015 | Goudra et al. |
| 2015/0359418 A1 | 12/2015 | Feussner et al. |
| 2016/0081712 A1 | 3/2016 | Heniford et al. |
| 2016/0166345 A1 | 6/2016 | Kumar et al. |
| 2016/0278611 A1 | 9/2016 | Power |
| 2016/0360954 A1 | 12/2016 | Rohling et al. |
| 2017/0055819 A1 | 3/2017 | Hansen et al. |
| 2017/0095269 A1 | 4/2017 | Reid et al. |
| 2017/0105802 A1 | 4/2017 | Taraschi et al. |
| 2017/0172382 A1* | 6/2017 | Nir .............. A61B 1/00045 |

(56) References Cited

U.S. PATENT DOCUMENTS

| | | | |
|---|---|---|---|
| 2017/0238962 | A1 | 8/2017 | Hansen et al. |
| 2018/0014851 | A1 | 1/2018 | Hansen et al. |
| 2018/0042686 | A1 | 2/2018 | Peine |
| 2018/0325604 | A1* | 11/2018 | Atarot .................. A61B 5/1114 |

FOREIGN PATENT DOCUMENTS

| | | |
|---|---|---|
| CN | 2691487 Y | 4/2005 |
| CN | 1729938 A | 6/2005 |
| CN | 201316257 Y | 9/2009 |
| CN | 201393995 Y | 2/2010 |
| CN | 201393999 Y | 2/2010 |
| CN | 201602746 U | 10/2010 |
| CN | 101991399 A | 3/2011 |
| CN | 201861616 U | 6/2011 |
| CN | 102401646 A | 4/2012 |
| CN | 102626301 A | 8/2012 |
| CN | 103299355 A | 9/2013 |
| CN | 203379100 U | 1/2014 |
| CN | 101305901 A | 4/2014 |
| CN | 203852327 U | 10/2014 |
| DE | 20002770 U1 | 10/2000 |
| DE | 102004008488 A1 | 9/2004 |
| DE | 102005045706 B3 | 4/2007 |
| DE | 102007007742 A1 | 8/2008 |
| DE | 102008056830 A1 | 5/2010 |
| DE | 202011103007 U1 | 11/2011 |
| DE | 102012209448 A1 | 12/2013 |
| DE | 102012209450 A1 | 12/2013 |
| EP | 2 412 290 A1 | 2/2012 |
| EP | 1961372 B1 | 3/2012 |
| EP | 2 554 103 A1 | 2/2013 |
| EP | 2 630 915 A1 | 8/2013 |
| EP | 2630915 A1 | 8/2013 |
| EP | 2551698 B1 | 9/2014 |
| EP | 3056934 A1 | 8/2016 |
| JP | 2000-131623 A | 5/2000 |
| JP | 2001-025469 A | 1/2001 |
| JP | 2003-061970 A | 3/2003 |
| JP | 2006-271600 A | 10/2006 |
| JP | 2015-073663 A | 4/2015 |
| WO | WO 95/10218 A1 | 4/1995 |
| WO | 00/42906 A2 | 7/2000 |
| WO | 01/52720 A1 | 7/2001 |
| WO | WO 02/080773 A1 | 10/2002 |
| WO | 2005/122940 A1 | 12/2005 |
| WO | 2009116969 A1 | 9/2009 |
| WO | WO 2009/116969 A1 | 9/2009 |
| WO | 2009134634 A1 | 11/2009 |
| WO | WO 2009/134634 A2 | 11/2009 |
| WO | 2012/072112 A1 | 6/2012 |
| WO | 2012/083247 A1 | 6/2012 |
| WO | WO 2012/083247 A1 | 6/2012 |
| WO | 2013/002050 A1 | 1/2013 |
| WO | 2013/096896 A1 | 6/2013 |
| WO | 2013/163391 A1 | 10/2013 |
| WO | WO 2013/163391 A1 | 10/2013 |
| WO | WO 2014/140813 A1 | 9/2014 |
| WO | 2014/174726 A1 | 10/2014 |
| WO | 2014/198675 A1 | 12/2014 |
| WO | 15124159 A1 | 8/2015 |
| WO | WO 2015/133958 A1 | 9/2015 |
| WO | WO 2015/135055 A1 | 9/2015 |
| WO | WO 2015/149041 A1 | 10/2015 |
| WO | 2016/019424 A1 | 2/2016 |
| WO | WO 2016/018815 A1 | 2/2016 |
| WO | WO 2016/057969 A2 | 4/2016 |

OTHER PUBLICATIONS

European Patent Application No. 16781653.7, by 3D Integrated ApS: Supplementary European Search Report, dated May 22, 2017 (4 pages).

Albitar, C. et al. (2007) "Robust Structured Light Coding for 3D Reconstruction" *Proceedings of the 2007 IEEE 11th International Conference on Computer Vision (ICCV 2007)*, Oct. 14-21, 2007, Rio de Janeiro, Brazil; pp. 1-6, DOI: 10.1109/ICCV.2007.4408982.

Edgcumbe, P. et al. (2014) "Pico Lantern: A Pick-up Projector for Augmented Reality in Laparoscopic Surgery" Medical Image Computing and Computer-Assisted Intervention (MICCAI) 17th International Conference, Boston, MA, USA, Sep. 14-18, 2014, Proceedings. P, Golland et al. (Eds.): *MICCAI 2014, Part 1, LNCS 8673*, pp. 432-439.

Hao, W. (Dec. 2011) *Wide Baseline Stereo Image Rectification and Matching*. Dissertation. The University of Tennessee, Knoxville, Tennessee; 175 pages.

Kang, H. (May 2002) *Robotic Assisted Suturing in Minimally Invasive Surgery*. Thesis. Rensselaer Polytechnic Institute, Troy, New York; 183 pages.

Krupa, A. et al. (2002) "Autonomous retrieval and positioning of surgical instruments in robotized laparoscopic surgery using visual servoing and laser pointers" *Proceedings of the 2002 IEEE International Conference on Robotics and Automation*, May 11-15, 2002, Washington, DC: vol. 4, pp. 3769-3774.

Louw, M. and F. Nicolls (2005) "An approximate EM Homographical Iterative Closest Point algorithm" PRASA2005, Langebaan, Cape Town; p. 89-92 [online]. Available from: http://dip.ee.uct.ac.za/~nicolls/publish/ml05-prasa.pdf.

Pellicanò, N. et al. (2016) "Robust Wide Baseline Pose Estimation from Video (Supplementary Material)" *Proceedings of the International Conference on Pattern Recognition (ICPR)*, Dec. 4-8, 2016; 2 pages.

Pritchett, P. and A. Zisserman (1998) "Wide Baseline Stereo Matching" *Proceedings of the Sixth International Conference on Computer Vision*, Jan. 4-7, 1998: pp. 754-760.

Reiter, A. et al. (2014) "Surgical Structured Light for 3D Minimally Invasive Surgical Imaging" *Proceedings of the IEEE/RSJ International Conference on Intelligent Robots and Systems (IROS 2014)*; pp. 1282-1287.

Zhang, K. et al. (Sep. 2009) "A Surface Topology and Motion Compensation System for Microsurgery Guidance and Intervention based on Common-Path Optical Coherence Tomography" *IEEE Trans Biomed Eng*, 56(9):2318-2321. NIH Public Access Author Manuscript; available in PMC Sep. 1, 2010 (12 pages).

Nicolau, S. (2011) "Augmented reality in laparoscopic surgical oncology" Surgical Oncology, pp. 189-201.

Hyunseok et al. (2015) "An effective visualization technique for depth perception in augmented reality surgical navigation" The International Journal of Medical Robotics and Computer-Assisted Surgery (May 5, 2015) doi: 10.1002/rcs. 1657.

Karjee et al, (2014) "Spatial Data Estimation in Three Dimensional Distributed Wireless Sensor Networks" Embedded System (ICES) 2014 International Conference (Jul. 3-4), IEEE ISBN 978-1-4799-5025-6.

International Search Report and Written Opinion for PCT/DK2016/050180 dated Apr. 11, 2016 (18 pages).

Salvi et al. (2004) "Pattern codification strategies in structured light systems" Pattern Recognition, vol. 37, Issue 4 (Apr.), pp. 827-849.

Ackerman, J.D. et al. (2002) "Surface reconstruction of abdominal organs using laparoscopic structured light for augmented reality" Proceedings of SPIE, 4661:39-46.

Bauer, S. et al. (2013) "Real-Time Range Imaging in Health Care: A Survey" in Time-of-Flight and Depth Imaging. Sensors, Algorithms, and Applications. Dagstuhl Seminar 2012 and GCPR Workshop on Imaging New Modalities. M. Grzegorzek et al. (Eds.) Springer Berlin Heidelberg. Lecture Notes in Computer Science, vol. 8200; pp. 188-212.

Clancy, N.T. et al. (2011) "Spectrally encoded fiber-based structured lighting probe for intraoperative 3D imaging" Biomedical Optics Express, 2(11):3119-3128.

European Patent Application No. 17169285.8 by 3dintegrated ApS: Extended European Search Report and European Search Opinion, dated Aug. 31, 2017 (7 pages).

Geng, J. (2011) "Structured-light 3D surface imaging: a tutorial" Advances in Optics and Photonics, 3:128-160.

(56) References Cited

OTHER PUBLICATIONS

Maier-Hein, L. et al. (2013) "Optical techniques for 3D surface reconstruction in computer-assisted laparoscopic surgery" [online]. Author deposited preprint: Retrieved from Sheffield Hallam University Research Archive (SHURA) at: htt..ilshura shu ac.ukI7180i; deposited on Aug. 2, 2013, 58 pages including cover. Final publication in: Medical Image Analysis, 17(8):974-996. (60 Pages).

Maier-Hein, L. et al. (2014) "Comparative Validation of Single-shot Optical Techniques for Laparoscopic 3D Surface Reconstruction" Accepted article, IEEE Transactions on Medical Imaging, doi: 10.1109/TMI.2014.2325607, 18 pages. Final publication in vol. 33, Issue 10, pp. 1913-1930, Oct. 2014.

Maurice, X. et al. (2013) "Real-time structured light coding for adaptive patterns" J. Real-Time Image Proc, 8:169-178.

Schmalz, C. et al. (2012) "An endoscopic 3D scanner based on structured light" Medical Image Analysis, 16:1063-1072.

Extended European Search Report received for European Patent Application No. 17884041.9, dated Aug. 12, 2020, 11 pages.

Pennington et al. (Jul. 2001) "Miniaturized 3-D Surface Profilometer using a Fiber Optic Coupler", Optics & Laser Technology, 33(5):313-320.

Schick et al. (May 26, 2011) "3D Measuring in the Field of Endoscopy", Proceedings of SPIE, 8082:808216-1-808216-12.

Su et al. (Aug. 26, 2015) "Three-dimensional Shape Measurements using Endoscopes", Proceedings of SPIE, 9586:95861H-1-95861H-6.

\* cited by examiner 3D data database system - classification data

| Unique code | M/F | Height (cm) | Weight (kg) | MIS cavity | Age | ⋯ |
|---|---|---|---|---|---|---|
| M-201 | M | 182 | 80 | Abdominal | 42 | ⋯ |
| F-325 | F | 171 | 60 | Pelvic | 76 | ⋯ |
| M-793 | M | 180 | 98 | Pericardial | 21 | ⋯ |
| ⋯ | ⋯ | 165 | ⋯ | ⋯ | 35 | ⋯ |
| ⋯ | | | | | | ⋯ |

Fig. 3

| 3D data database system - 3D data sets | | | |
|---|---|---|---|
| Unique code | 3D data set -surface a | 3D data set -surface b | ... |
| M-201 | Data... | Data... | ... |
| F-325 | Data... | Data... | ... |
| M-793 | Data... | Data... | ... |
| ... | Data... | Data... | ... |
| ... | ... | ... | ... |

Fig. 4

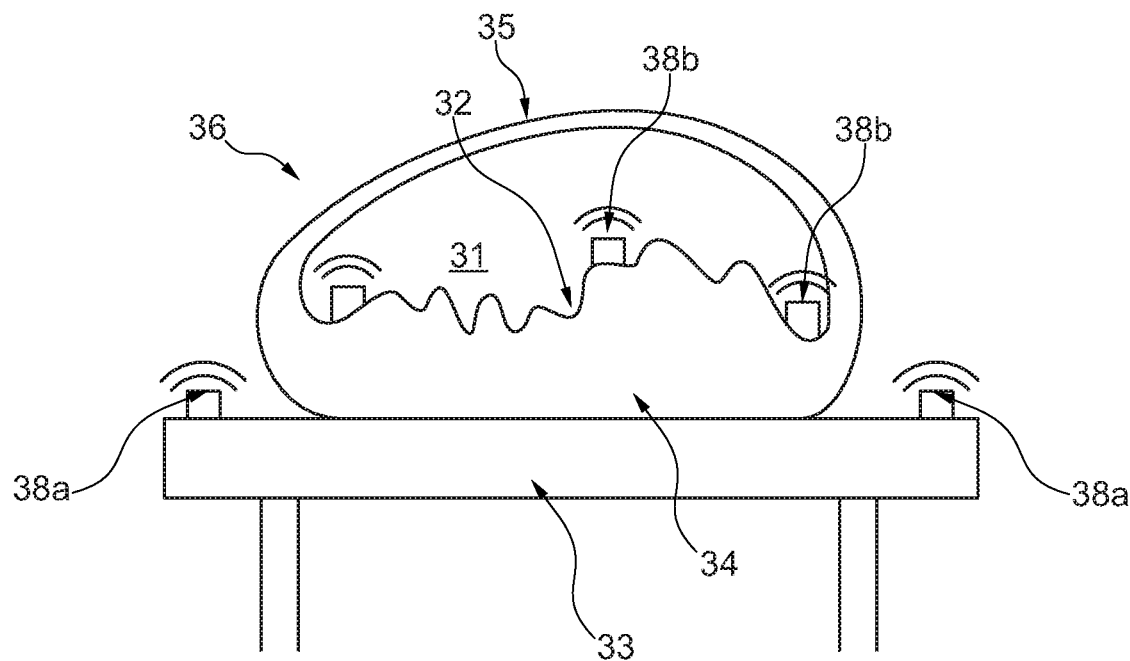
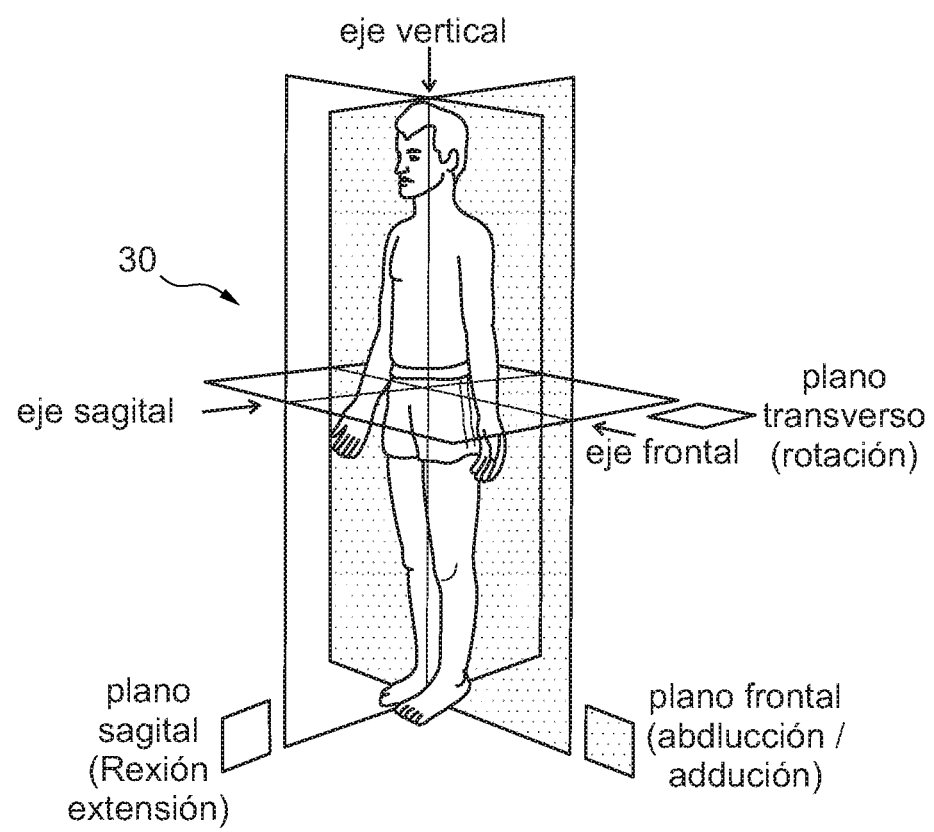
Fig. 7

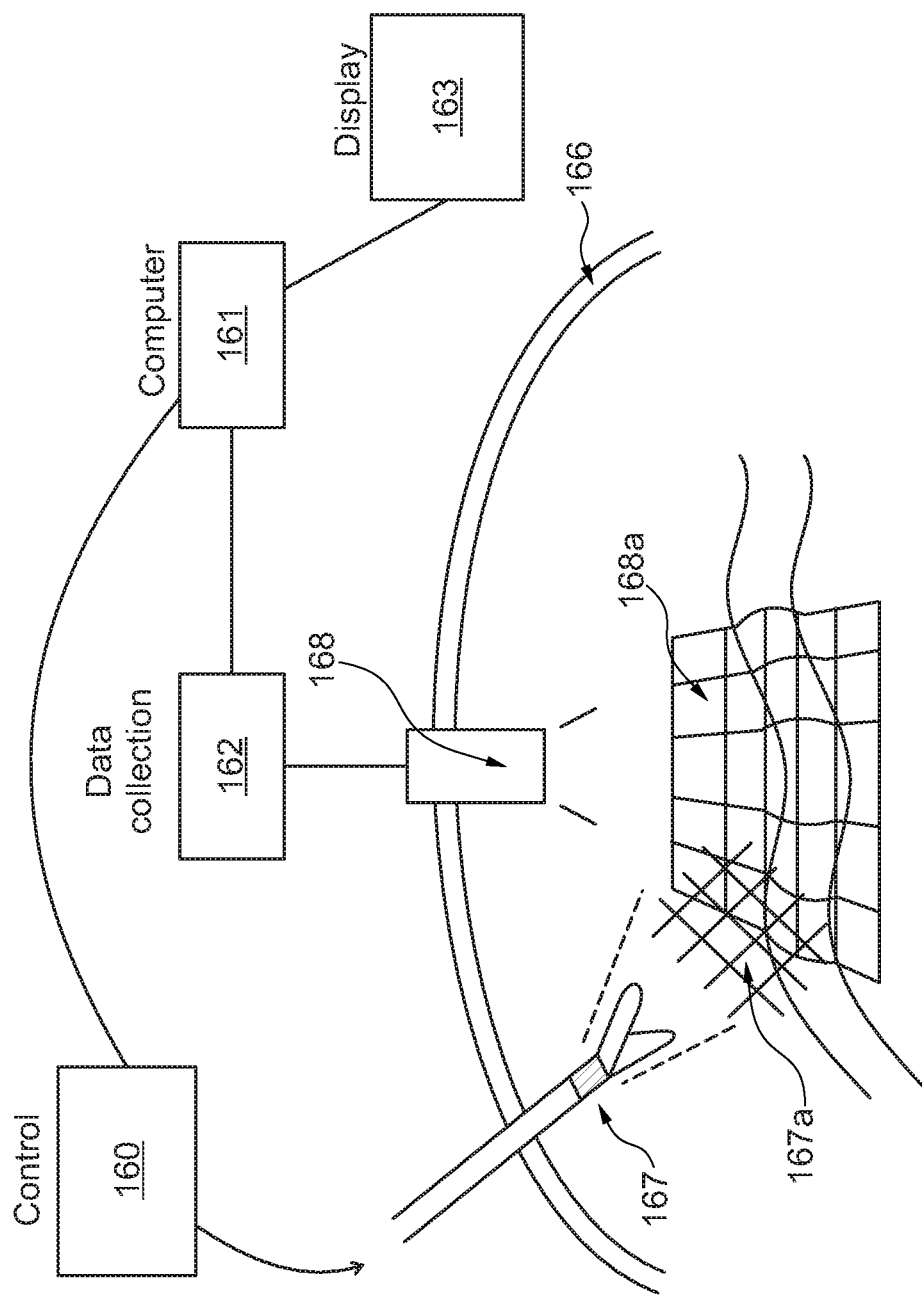

REAL TIME CORRELATED DEPICTION SYSTEM OF SURGICAL TOOL

This is a continuation of International Application PCT/DK2016/050180, with an international filing date of Jun. 13, 2016 and claiming priority from PA 2015 70642 DK of Oct. 9, 2015. International Application PCT/DK2016/050180 is hereby incorporated by reference.

TECHNICAL FIELD

The invention relates to a depiction system for generating a real time depiction of movements of a surgical tool during a minimally invasive surgery and adapted for in real time providing a surgeon with information, such as information about the position of the surgical tool.

BACKGROUND ART

Minimally invasive surgery has been used increasingly in recent years due to the benefits compared to conventional open surgery as it reduces the trauma to the patient tissue, leaves smaller scars, minimizes post-surgical pain and enables a faster recovery of the patient.

For example, in laparoscopic surgery which is a typical form of minimally invasive surgery the surgeon accesses a body cavity, such as the abdominal or pelvic cavity, through a series of small incisions. A laparoscope is inserted through an incision, and conventionally connected to a monitor, thereby enabling the surgeon to see the inside of the abdominal or pelvic cavity. In order to perform the surgical procedure, surgical instruments are inserted through other incisions. In addition, the body cavity around the surgical site is inflated with a fluid, preferably gas e.g. carbon dioxide in order to create an 'air' space within the cavity to make space for the surgeon to view the surgical site and move the laparoscopic instruments.

Invasive surgery procedures are generally performed through openings in a patient's skin—often relatively small openings—and the surgical site is visualized for the surgeon by inserting a camera, such as an endoscope into the body cavity and displaying the images on a screen.

In order to improve the vision for surgeon, in particular to make it easier for the surgeon to determine the sizes of various organs, tissues, and other structures in a surgical site, several in-situ surgical metrology methods have been provided in the prior art. Different types of optical systems have been applied to provide an improved vision of the surgical site, which is approaching a 3D vision.

US 2013/0296712 describes an apparatus for determining endoscopic dimensional measurements, including a light source for projecting light patterns on a surgical sight including shapes with actual dimensional measurements and fiducials, and means for analyzing the projecting light patterns on the surgical site by comparing the actual dimensional measurements of the projected light patterns to the surgical site.

WO 2013/163391 describes at system for generating an image, which the surgeon can use for measuring the size of or distance between structures in the surgical field by using an invisible light for marking a pattern to the surgical field. The system comprises a first camera; a second camera; a light source producing light at a frequency invisible to human eye; a dispersion unit projecting a predetermined pattern of light from the invisible light source; an instrument projecting the predetermined pattern of invisible light onto a target area; a band pass filter directing visible light to the first camera and the predetermined pattern of invisible light to the second camera; wherein the second camera images the target area and predetermined pattern of invisible light, and computes a three-dimensional image.

US2008071140 discloses an endoscopic surgical navigation system comprises a tracking subsystem to capture data representing positions and orientations of a flexible endoscope during an endoscopic procedure, to allow co-registration of live endoscopic video with intra-operative and/or pre-operative scan images. Positions and orientations of the endoscope are detected using one or more sensors and/or other signal-producing elements disposed on the endoscope.

US2010268067 disclose methods, systems, devices, and computer-readable media for image guided surgery for allowing a physician to use multiple instruments for a surgery and simultaneously provide image-guidance data for those instruments.

US2011069159 discloses a system for orientation assistance and display of an instrument that is inserted or present in the natural or artificially produced hollow cavity (human, animal, object), and that is equipped with one or more sensor units. Multiple measurements of the 3D position of the instrument equipped with one or more sensor units are performed by positioning a measuring system, so that a precise orientation and positioning of the instrument in the body can be computed. The 3D position data are used to compute a virtual image of the instrument synchronously. The virtual images are then either projected directly in exact position onto the body surface of a person or combined in a body surface image (real video camera image of the patient) onto a monitor or superimposed (virtual or augmented reality).

It has also been suggested to generate augmented reality vision of surgery cavities for providing an improved view of internal structures of patient organs of to determine minimally distance to a cavity surface or organ of a patient. Such systems are described in the articles "Augmented reality in laparoscopic surgical oncology" by Stéphane Nicolau et al. Surgical Oncology 20 (2011) 189-201 and "An effective visualization technique for depth perception in augmented reality-based surgical navigation" by Choi Hyunseok et al. The international journal of medical robotics and computer assisted surgery, 2015 May 5. doi: 10.1002/rcs.1657.

US2014163359 discloses a surgical tracking system for assisting an operator to perform a laparoscopic surgery of a human body. The surgical tracking system comprising: a) at least one endoscope adapted to acquire real-time images of a surgical environment within said human body; b) a maneuvering subsystem adapted to control the spatial position of said endoscope during said laparoscopic surgery; and, c) a tracking subsystem in communication with said maneuvering subsystem, adapted to control the maneuvering system so as to direct and modify the spatial position of said endoscope to a region of interest. The system generates real life correlated images of movement of a surgical tool.

DISCLOSURE OF INVENTION

In an embodiment of the depiction system of the invention the system provides an alternative system for generating good visibility of at least a part of a body cavity during minimally invasive surgery in particular with respect to providing good visual information to the surgeon about the position of a surgical instrument relative to the surgical site.

The depiction system of the invention has shown to be capable of providing a surprisingly good visibility to a user, such as a surgeon or a person training for performing a surgery. In an embodiment the system of the present invention aims to provide a depiction comprising a projection of the position of a surgical tool rather than imaging the surgical tool. Thereby the user can be provided with a large amount of information in one single depiction. Whereas one single depiction can provide the use with large amount of information, the invention also comprises a system generating two or more depictions or images as further described below.

The depiction system of the invention is suitable for generating a real time correlated depiction of movements of a surgical tool.

The system comprising
a computer system configured for being in data communication with a display unit,
3D surface data generation means for providing the computer system with three-dimensional (3D) data representing at least one surface section in 3D space of a minimally invasive surgery cavity, wherein the surface section comprises a target area, and
position data generation means for obtaining real time spatial position data of at least a part of the surgical tool and for transmitting the obtained spatial position data to the computer system.

At least one of the 3D surface data generation means and the position data generation means comprises surface position data generation means for providing surface position data of at least the target area.

The computer system is programmed for
determining a 3D surface contour of at least a part of the target area of the surface section of the minimally invasive surgery cavity using the 3D data,
determining real time spatially position(s) of the surgical tool relative to at least a part of the target area of the at least one surface section using the spatial position data and the surface position data,
calculating depiction data representing a depiction of the real time relative spatial position(s) of the surgical tool onto at least a portion of the surface contour of the surface section of the minimally invasive surgery cavity, and for
transmitting the depiction data to the display unit for real time correlated depiction of movements of the surgical tool.

The computer system may comprise one single computer or a plurality of computers in data connection, wireless, by wire and/or via the internet.

The minimally invasive surgery cavity may be a patient or an artificial cavity. In general, an artificial cavity is useful in a training procedure. In other procedures as well as in supervised procedures of relatively unexperienced surgeons the minimally invasive surgery cavity is advantageously a minimally invasive surgery cavity of a patient such as a human or an animal.

The minimally invasive surgery cavity may in principle be any kind of body cavities including naturally occurring cavities as well as cavities formed by expansion of a non-luminal part of a body (pseudo cavity). Examples of suitable minimally invasive surgery cavities includes an abdominal cavity (the area between the diaphragm and the brim of the pelvis), a chest cavity, abdominopelvic cavity (contains both the abdominal and pelvic cavities), cranial cavity (contains the brain), diaphragm (muscle that separates the thoracic and abdominopelvic cavities), mediastinum (central area within the thoracic cavity), pelvic cavity (contains the reproductive organs and urinary bladder), pericardial cavity (contains the heart), pleural cavity (contains the lungs), thoracic cavity (enclosed by the ribs, sternum, and vertebral column), vertebral cavity (contains the spinal cord), etc.

Usually the minimally invasive surgery procedure includes that the surgeon provides access to the surgery site by an incision and apply a cannula (sometimes also called a sleeve) to provide an access port through the incision. The cannula functions as a portal for the subsequent placement of a surgical instrument comprising a surgical tool. The term 'surgical tool' is herein used to designate the distal part of a surgical instrument adapted to be inserted into the minimally invasive surgery cavity. A surgical instrument usually has a distal end and a proximal end and comprises a handle portion at its proximal end, a surgical tool at its distal end and a body portion connecting the handle portion to the surgical tool. The surgical tool may for example be graspers, scissors, staplers, etc. In an embodiment the body portion of the surgical instrument is considered as a part of the surgical tool. For examples sensors mounted to the surgical tool portion may be mounted to the body portion of the surgical instrument.

The cannula usually comprises one or more seals to seal against gas slip-out and to accommodate an instrument. After the cannula has been inserted, the minimally invasive surgery cavity is usually enlarged by blowing a gas into the cavity thereby providing a cavity sufficiently large for performing the minimally invasive surgery procedure.

Often the surface of the minimally invasive surgery cavity is much curved. The term 'target area' of the surface of the minimally invasive surgery cavity is herein used to designate the area which the surgeon has focus on, and the target area may advantageously comprise a surgery site and/or a surface area which potentially could be in risk of damage during the surgery procedure for example a critical structure, such a vene structure. The depiction data representing said depiction of said real tile spatial positions of the surgical tool onto at least a portion of the surface contour of the surface section of the minimally invasive surgery, where the portion of the surface contour need not comprise the surface contour of the target area constantly during a minimally invasive surgery procedure. It is sufficient that the contour of the target area forms part of the portion of the surface contour when the surgical tool is approaching the target area.

In an embodiment depiction system is configured for determining real time spatial position data comprising determining a distance from the surgical tool to a critical structure of the surface section.

The phrase "real time" is herein used to mean the time it requires the computer to receive and process constantly changing data optionally in combination with other data, such as predetermined data, reference data, estimated data which may be non-real time data such as constant data or data changing with a frequency of above 1 minute to thereby provide a depiction of corresponding actual changes as they occur or within up to 5 seconds, preferably within 1 second, more preferably within 0.1 second of occurrence.

The terms distal and proximal should be interpreted in relation to the orientation of the surgical tool i.e. the distal end of the surgical tool is the part of the surgical tool farthest from the incision through which the surgical instrument comprising the surgical tool is inserted.

The phrase "distal to" means "arranged at a position in distal direction to the surgical tool, where the direction is determined as a straight line between a proximal end of the surgical tool to the distal end of the surgical tool. The phrase "distally arranged" means arranged distal to the distal end of the surgical tool.

The term "substantially" should herein be taken to mean that ordinary product variances and tolerances are comprised.

The term "about" is generally used to ensure that what is within measurement uncertainties are include. The term "about" when used in ranges, should herein be taken to mean that what is within measurement uncertainties are included in the range.

It should be emphasized that the term "comprises/comprising" when used herein is to be interpreted as an open term, i.e. it should be taken to specify the presence of specifically stated feature(s), such as element(s), unit(s), integer(s), step(s) component(s) and combination(s) thereof, but does not preclude the presence or addition of one or more other stated features.

Throughout the description or claims, the singular encompasses the plural unless otherwise specified or required by the context.

The portion, i.e. the area extension of the surface contour which is comprised in the depiction data calculation may in principle have any size larger than zero. In order to provide a depiction containing desirably large amount of information for the user, the portion of the surface contour advantageously has a size which is sufficiently large to reflect the surface contour of the portion. In an embodiment the portion of the surface contour has a size of at least about 5 $mm^2$, such as at least about 10 $mm^2$, such as at least about 1 cm2, such as at least about 5 $cm^2$, such as at least about 10 $cm^2$, such as at least about 25 $cm^2$ determined as the maximal size of a projection of the surface contour onto a plan—i.e. the plan is selected as the plan providing the largest projected surface. In an embodiment the portion of the surface contour has a size as least as large as the target area and/or as least as large as the surgical site.

Advantageously the portion of the surface contour which is comprised in the depiction data calculation has a size which is dynamically changing in dependence of the real time position data, Thereby the depiction may reveal any movements of the surgical tool.

In an embodiment the portion of the surface contour is increasing with increasing distance between the spatial position the part of the surgical tool and the surface section.

In an embodiment the 3D surface data generation means and/or the position data generation means is/are part of the depiction system and advantageously the 3D surface data generation means and/or the position data generation means is/are controlled by the computer system. The computer system is preferably programmed to control the operation of the 3D surface data generation means and/or the position data generation means.

The 3D surface data generation means may be any means capable of providing the computer system with the 3D surface data, such as data from a database, data supplied to the computer system by a user, e.g. in form of pre-measured data e.g. by scanning e.g. CT scanning e.g. MR or real-time measured data.

In an embodiment the 3D surface data generation means comprises a 3D database system. The 3D database system comprises at least one 3D data set for at least one surface section of each of a plurality of classified minimally invasive surgery cavities, wherein each 3D data set is associated to the respective surface section(s) of at least one of the classified minimally invasive surgery cavities. Preferably the computer is configured for acquiring a 3D data set for at least one surface section of a classified minimally invasive surgery cavity.

The classified minimally invasive surgery cavities are preferably represented by their respective classification. The classification may in principle comprise any classification data that describes the classified minimally invasive surgery cavities e.g. type of cavity, age of patient, weight of patient, gender of patient, height, body circumferential dimension(s) or any combinations comprising the abovementioned or any other specific or average or level of patient data.

In an embodiment the computer is programmed to receive instructions for selecting a 3D data set and based on an instruction to acquire the selected 3D data set from the 3D database. The instruction may advantageously comprise classification data. The instruction may for example be given to computer system via a digital user interface and/or orally by a user.

Unless otherwise stated, the term "user" is herein used to include any user, such as a surgeon, an assisting surgeon, a supervisor, a computer programmed to act as supervisor, an artificially intelligent computer and/or a robot, where a robot is programmed to perform at least one surgeon duty, e.g. to perform or assist in a minimally invasive surgery procedure.

In an embodiment the surgeon is a robotic surgeon.

In an embodiment the visual information means optical data as received by a robotic surgeon and representing a surface section of the minimally invasive surgery cavity.

In an embodiment the computer is programmed to receive instructions comprising classification data for selecting several 3D data sets and based on this instruction to acquiring selected 3D data sets and process the acquired 3D data sets to determine the resulting 3D data which is applied to determine the 3D surface contour of the surface section of the minimally invasive surgery cavity.

In an embodiment the computer is programmed to receive instructions comprising classification data for selecting several 3D data sets and based on this instruction to acquiring selected 3D data sets and processing the acquired 3D data sets to determine the resulting 3D data which is applied to determine the 3D surface contour of the surface section of the minimally invasive surgery cavity.

The database system is data connectable or in data connection with the computer e.g. by wireless connection, by wire connection, via the internet and/or by being loaded onto a memory of the computer system.

The database system may continuously be build up or updated by adding new 3D data sets to the database.

In an embodiment the database system is loaded into a memory in data communication with or being a part of the computer system.

The 3D data sets of the database may be obtained by any methods and will usually be 3D data sets from previously performed minimally invasive surgery procedures and/or estimated and/or calculated 3D data sets and/or 3D data sets obtained by a scanning such as described further below.

Advantageously one or more of the 3D data sets comprises estimated 3D data, calculated 3D data, measured 3D data or any combination thereof. Preferably the 3D data sets each are associated to a patient characteristic, such as a patient characteristic comprising age, gender, weight, height body circumferential dimension(s) or any combinations comprising the abovementioned.

The estimated 3D data, calculated 3D data and/or measured 3D data of the 3D data sets may be obtained or generate by any methods, such as methods known from prior art and/or methods described herein for obtaining 3D data a surface section of a minimally invasive surgery cavity. In particularly ultra sound based methods, CT scanning and/or MRI are suitable as well as the prior art methods as disclosed in the articles "Augmented reality in laparoscopic surgical oncology" by Stéphane Nicolau et al. Surgical Oncology 20 (2011) 189-201 and "An effective visualization technique for depth perception in augmented reality-based surgical navigation" by Choi Hyunseok et al. The international journal of medical robotics and computer assisted surgery, 2015 May 5. doi: 10.1002/rcs.1657.

In an embodiment the 3D surface data generation means comprises a user input data connection for feeding 3D data for a selected patient onto the computer. The computer is configured for receiving such user input 3D data, optionally by comprising a reader configured for reading images e.g. 2D and/or 3D and comprising software generating the 3D data from the read images. Advantageously the user input 3D data is added as 3D data set to the database system.

In an embodiment the 3D surface data generation means comprises a 3D surface sensor system for determining at least a part of the 3D data for at least the surface section of the minimally invasive surgery cavity and transmitting means for transmitting the determined for 3D data to the computer, optionally depiction system is configured for adding determined 3D data as 3D data set to the database system. Preferably the computer system is configured for adding determined 3D data received from the 3D surface sensor system as 3D data set to the database system.

In an embodiment the sensor system is adapted for determining at least a part of the 3D data for at least the surface section of the minimally invasive surgery cavity and the sensor system is further configured for generating at least one of pre-operative data and/or intra-operative data.

The transmitting means may be any means suitable for transmitting said 3D data, preferably in digital form. Suitable transmitting means includes USB key transmitting means, wire based transmitting means and/or wireless transmitting means, such as Bluetooth.

The surface sensor system may comprise any type of surface sensor suitable for determining 3D data of the surface section. In a preferred embodiment the 3D surface sensor system comprises at least one local reference sensor, preferably for spatial reference. Advantageously the at least one local reference sensor is adapted to be positioned on a patient and/or on a support (surgery table) for a patient.

In an embodiment there are a plurality of reference sensors, the reference sensors are preferably configured to communicate to locate a position of each other to thereby define an X.Y.Z dimensional space—e.g. as describes in US 2007/060098 or U.S. Pat. No. 6,631,271. In an embodiment the 3D surface sensor system is as described in "Spatial Data Estimation in Three Dimensional Distributed Wireless Sensor Networks", by Karjee et al. Embedded Systems (ICES), 2014 International Conference 3-4 Jul. 2014, IEEE ISBN 978-1-4799-5025-6.

In an embodiment the 3D surface data generation means comprises the surface position data generation means for providing surface position data of the target area. The surface position data generation means advantageously comprises the at least one local reference sensor described above.

The 3D surface sensor system may advantageously comprise a 3D optical sensor, an acoustic sensor, a magnetic sensor, an electric sensor, an electromagnetic sensor or any combinations thereof.

In an embodiment the 3D surface sensor system comprises a surface tracking system as described in "Augmented reality in laparoscopic surgical oncology" by Stéphane Nicolau et al. Surgical Oncology 20 (2011) 189-201.

The one or more sensors of the sensor system can in principle be positioned anywhere as long as it is capable of sensing at least a part of the surface section. Advantageously the one or more sensors of the sensor system is/are part of the depiction system. Where the one or more sensors of the sensor system is/are fixed to or integrated with one or more elements, this/these one or more elements advantageously form part of the depiction system.

In an embodiment at least one sensor is positioned on or is adapted to be positioned on a trocar and/or cannula, the trocar and/orcannula is preferably a part of the depiction system. In an embodiment at least one sensor is positioned on or is adapted to be positioned on a surgical instrument, preferably on a surgical tool of the surgical instrument for use in minimally invasive surgery, the surgical instrument or the surgical tool is preferably a part of the depiction system. In an embodiment at least one sensor is positioned on or is adapted to be positioned on an endoscope for use in minimally invasive surgery, the endoscope is preferably a part of the depiction system. In an embodiment at least one sensor is positioned on or is adapted to be positioned on a patient e.g. in the minimally invasive surgery cavity, such as on a surface thereof or external on the surface of the skin of a patient. In an embodiment at least one sensor is positioned on or is adapted to be positioned on a sensor instrument which can be at least partly inserted into the minimally invasive surgery cavity, the sensor instrument is preferably a part of the depiction system. In an embodiment at least one sensor is adapted to be positioned external to the minimally invasive surgery cavity e.g., to be manually handled or handled by a robot, preferably the external sensor (e.g. a scanning instrument—CT, NMR, MR, UV and/or IR scanner) and optionally the robot form part of the depiction system.

In an embodiment the 3D surface sensor system comprises a 3D optical sensor system comprising at least one optical source and at least one optical reader such as an image recorder comprising a 2D array of detectors, such as a camera, the 3D optical sensor system is preferably a binocular sensor system or a multiocular sensor system.

The optical source of the 3D optical sensor source may in principle comprise any kind of optical source, such as an illumination source, an invisible source—e.g. an IR source.

The optical source may be a coherent light source or an incoherent light source. Examples of optical sources includes a semiconductor light source, such as a laser diode and/or a VCSEL light source as well as any kind of laser sources including narrow bandwidth sources and broad band sources.

In an embodiment the optical source has a band width (full width at half maximum—FWHM) of up to about 50 nm, such as from 1 nm to about 40 nm. Preferably the narrow band width of the optical source is about 25 nm or less, such as about 10 nm or less.

In an embodiment the optical source is a broad band light source such as a supercontinuum light source e.g. spanning at least an octave within the bandwidth range from 400 nm to 2600 nm. Above 2600 nm light transmitted in a silica fiber will be strongly attenuated.

In an embodiment the optical source is configured for emitting at least one electromagnetic wavelength within the UV range of from about 10 nm to about 400 nm, such as from about 200 to about 400 nm.

In an embodiment the optical source is configured for emitting at least one electromagnetic wavelength within the visible range of from about 400 nm to about 700 nm, such as from about 500 to about 600 nm.

In an embodiment the optical source is configured for emitting at least one electromagnetic wavelength within the IR range of from about 700 nm to about 1 mm, such as from about 800 to about 2500 nm.

In an embodiment the optical source comprises at least one wavelength within the invisible range, such as the UV or the IR range.

Advantageously the optical source is tunable in wavelength and/or power.

The optical source is advantageously connected to or integrated in an endoscope.

In an embodiment the 3D optical sensor system comprise two optical sources, preferably laser sources of equal or different wavelength(s) and being emitted towards the surface in different light beam angles (determined as the angle of the centremost ray of the respective light beams).

In an embodiment the 3D optical sensor system is based on USING BEAM PHASE interference determination e.g. as described in US2004/0145746.

In an embodiment the 3D optical sensor system may for example comprise a phase optic element (e.g. a diffractive optic element (DOE)), a spatial light modulator, a multi-order diffractive lens, a holographic lens, a Fresnel lens and/or a computer regulated optical element. In an embodiment the DOE is as described in US 2013/0038836 e.g. as shown in FIG. 1 and/or as described in section [0015] of US 2013/0038836.

In an embodiment the 3D optical sensor system comprises two cameras e.g. as described in WO 2013/163391.

In an embodiment the at least one optical source is configured for emitting an optical tracking light pattern which pattern when impinged onto and reflected and/or scattered from the surface reveal the contour of the surface to thereby provide 3D data to be recorded by the optical reader. In this embodiment the 3D optical sensor system may advantageously be or comprise the apparatus described in US 2013/0296712 and/or EP 2 586 34.

In an embodiment at least one of the optical pattern emitting source and the recorder is positioned on an endoscope which advantageously forms part of the system.

In an embodiment the optical source is adapted for emitting a substantially stationary optical pattern onto at least a part of the surface section which pattern when impinged onto and reflected and/or scattered from the surface reveal the contour of the surface to thereby provide 3D data to be recorded by the optical reader and the optical pattern emitting source optionally being positioned on an endoscope which is adapted to be held substantially stationary during the minimally invasive surgery procedure, such as on an endoscope also comprising the recorder.

In the following the term "reflected and/or scattered from a surface" should be interpreted to include any interactions with the relevant surface which is readable by an optical recorder. The light in question may be visibly or invisible to the human eye e.g. including wavelengths from below 300 nm to above 2 μm.

Advantageously the depiction system preferably comprises both a stationary and a dynamic optical pattern source. The dynamic optical pattern source is preferably in form of a light source adapted for emitting said dynamic optical pattern onto at least a part of the surface section. The dynamic optical pattern is preferably dynamic by being mounted onto a surgical tool such that the reflected and/or scattered pattern (the pattern reflected and/or scattered from the surface section), which may be recorded by the recorder is changing in relation to movements of the surgical tool. Preferably the changes of the reflected and/or scattered pattern are correlated to the movements of the surgical tool. The correlated movement of the pattern may e.g. be provided as described in WO 15/124159 e.g. comprising the set comprising a surgical instrument wherein the surgical tool as described herein includes the body and the surgical tool of the surgical instrument of WO 15/124159. The correlated movement of the pattern may e.g. be provided as described in DK PA 2015 70483. The optical recorder may be mounted on the surgical tool and/or on an endoscope or at any other suitable means.

The optical source may be temporarily or permanently fixed to the surgical tool and the optical source preferably also form part of the position data generation means.

By simultaneously use of the a stationary and a dynamic optical pattern source both the 3D data—or at least some of the 3D data optionally supplemented with one or more 3D data set(s) from the 3D database system—and the real time position data can be generated simultaneously.

In an embodiment the depiction system comprises a dynamic optical pattern preferably dynamic by being mounted onto a surgical tool as described above and simultaneously the system comprises an optical recorder mounted to the surgical tool or to an endoscope for collecting both 3D data and position data and preferably orientation data.

In an embodiment the 3D surface sensor system comprises an acoustic sensor system comprising at least one sonic wave emitter and at least one sonic wave receiver. Preferably the acoustic sensor system comprises two or more sonic wave receivers, such as a 2D array of sonic wave receivers e.g. piezo sonic wave receivers.

Advantageously the acoustic sensor system comprises an ultrasound sensor. The 3D optical sensor system may e.g. be as described in any one of U.S. Pat. No. 4,694,434 of US 2014/0204702.

In an embodiment the 3D surface sensor system comprises a magnetic sensor system, such as a magnetic induction tomography sensor system and/or a magnetic resonance tomography sensor and/or an electromagnetic sensor system.

In an embodiment the 3D surface sensor system comprises an electric sensor system, such as a micro mechanical sensor system.

In an embodiment the 3D surface sensor system comprises an X-ray computed tomography sensor (CT scanning sensor).

The position data generation means may be any kind of position data generation means suitable for determining the real time spatial position of at least a part of the surgical tool. Preferably the part of the surgical tool includes at least the distal end of the tool.

In an embodiment the position data generation means for obtaining real time spatial position data of at least a part of the surgical tool comprises a position sensor system. The position sensor system preferably comprises a 3D optical sensor, an acoustic sensor, a magnetic sensor, an electric sensor, an electromagnetic sensor, an accelerometer, a gyroscope, a gravimeter an inertial navigation system a local positioning system or any combinations thereof.

Advantageously the position sensor system is part of the depiction system.

In an embodiment the position sensor system comprises an inertial navigation system. The inertial navigation system advantageously includes at least a computer (e.g. of the computer system) and a platform or module containing accelerometers, gyroscopes and/or other motion-sensing devices. The inertial navigation system may initially be provided with its position and velocity from another source (such as a human operator, a GPS satellite receiver, etc.), and thereafter computes its own updated position and velocity by integrating information received from the motion sensors. The advantage of an inertial navigation system is that it requires no external references in order to determine its position, orientation, or velocity once it has been initialized.

In an embodiment the position sensor system comprising a sensor element adapted to be or being physically connected to or integrated with the surgical tool.

In an embodiment the position sensor system comprises a magnetic motion capture systems comprising at least one sensor adapted to be or being physically connect to or integrated with the surgical tool to measure low-frequency magnetic fields generated by a transmitter source.

In an embodiment the position sensor system comprises a MEMS sensor magnetic motion capture systems adapted to be or being physically connect to or integrated with the surgical tool to measure return signal upon activation by a transponder.

In an embodiment the position sensor system comprises an acoustic sensor including at least one sensor mounted on integrated with the surgical tool the surgical tool for increase accuracy—e.g. for direction determination.

The one or more sensors of the position sensor system may advantageously be positioned as described above for the sensor(s) of the 3D sensor system optionally with an additional sensor mounted on or integrated with the surgical tool. Advantageously one or more sensors may be part of both the 3D sensor system and the position sensor system.

In an embodiment the position sensor system comprises at least one local reference sensor, preferably for spatial reference. The at least one local reference sensor is preferably adapted to be positioned on a patient, such as in the minimally invasive surgery cavity or on the outer skin of the patient and/or on a support (e.g. a surgery table) for a patient.

In an embodiment the position sensor system comprises a plurality of reference sensors—preferably also being a part of the 3D surface sensor system. The reference sensors are preferably configured to communicate to locate a position of each other to thereby define an X.Y.Z dimensional space— e.g. as describes in US 2007/060098 or U.S. Pat. No. 6,631,271. In an embodiment the position sensor system is based on the technology described in "Spatial Data Estimation in Three Dimensional Distributed Wireless Sensor Networks", by Karjee et al. Embedded Systems (ICES), 2014 International Conference 3-4 July 2014, IEEE ISBN 978-1-4799-5025-6.

In an embodiment the at least one reference sensor provides the local positioning system, preferably the position sensor system comprises a plurality local reference sensors.

The position sensor system is advantageously configured for obtaining real time spatial position data of the surgical tool and for transmitting the obtained spatial position data to the computer system, wherein the real time spatial position data is on form of real time spatial position data in an X-Y-Z dimensional space.

In an embodiment the position sensor system comprises at least one distance sensor, such as a short range laser based sensor e.g. as provided by SICK AG, Germany.

A short range laser based distance sensor is operating by projecting a light beam spot onto a measurement object, e.g. using a laser diode. By means of an optical receiver, the reflection is mapped onto a light sensitive element (such as CMOS). Based on the position of the mapped light spot and the 3D surface data, the distance to the surface section can be determined.

Advantageously the real time spatial position data comprises position data correlated to the 3D data representing at least one surface section in 3D space, preferably the real time spatial position data comprises determining a distance from the surgical tool or the at least one part of the surgical tool to the surface section, preferably to the target area of the surface section.

In an embodiment the real time spatial position data comprises determining a distance e.g. using a short range laser based distance sensor from the surgical tool or at least one part of the surgical tool—preferably its distal end—and to a point of the surface section correlated with an orientation direction of the tool, where the orientation direction of the tool is determined from an access opening into the minimally invasive surgery cavity through which the tool is inserted and the farthest extension of the tool into the cavity. This orientation direction is also referred to as the longitudinal vector direction of the surgical tool and/or where the surgical tool is not bended or bendable—the longitudinal direction of the surgical tool. Where the surgical tool is bended the longitudinal direction is determined as the direction of the distal part of the surgical tool from the bend to the most distal part of the tool.

In an embodiment the real time spatial position data comprises determining a distance from the surgical tool or at least one part of the surgical tool—preferably its distal end—and to a point of the surface section in distal direction to the surgical tool.

Advantageously the 3D surface sensor system and the position sensor system are at least partly integrated to form a combined 3D surface and position sensor system. Preferably this 3D surface and position sensor system is a part of the depiction system.

In an embodiment the computer system is in data connection with the 3D surface data generation means and is configured for acquire the 3D data representing at least one surface section in 3D space of a minimally invasive surgery cavity from the 3D surface data generation means. Preferably the computer system is configured for receiving instruction via a user interface to acquire the 3D data and upon receiving such instructions to acquire the 3D data.

In an embodiment the computer system—for each user procedure—is configured to acquire the 3D data representing at least one surface section in 3D space of a minimally invasive surgery cavity in one single time data package. In this embodiment the acquired 3D data representing at least one surface section in 3D space of a minimally invasive surgery cavity may be used in the whole minimally invasive surgery procedure, and the 3D surface data generation means is advantageously controlled by the computer system to acquire the 3D data representing at least one surface section in 3D space of a minimally invasive surgery cavity only once in one data package.

In another embodiment the computer system—for each user procedure—is configured for acquiring the 3D data by consecutively acquiring 3D data packages representing at least one surface section in 3D space of a minimally invasive surgery. The consecutively acquired 3D data packages preferably comprises timely updated 3D data and/or 3D data representing at least one additional surface section in 3D space for each of the consecutive acquired 3D data packages. Advantageously the operation of the 3D surface data generation means is controlled by the computer system.

In an embodiment the computer system is in data communication with the position data generation means and is configured for in real time acquire the obtained real time spatial position data of at least a part of the surgical tool.

Preferably the computer system is configured for receiving instruction via a user interface to acquire the spatial position data and upon receiving such instructions to acquire the spatial position data.

In an embodiment the computer system is configured for controlling the 3D surface data generation means and the position data generation means. Preferably the computer is configured for receiving instruction via a user interface to conduct a user process and based on the instruction to acquire the required data from the 3D surface data generation means and the position data generation means and for conducting the user procedure until a termination signal is transmitted to the computer.

Advantageously the system further comprises orientation data generation means for obtaining real time spatial orientation data of at least a part of the surgical tool and for transmitting the obtained spatial orientation data to the computer system. The computer system is advantageously programmed for determining real time spatially orientation(s) of the surgical tool using the spatial orientation data, calculating depiction data representing a depiction of the real time spatial orientation(s) of the surgical tool onto at least a portion of the surface contour of the surface section of the minimally invasive surgery cavity, and for transmitting the depiction data to the display unit for real time correlated depiction of movements of the surgical tool.

Advantageously the computer system is configured to calculating depiction data representing the depiction of the real time relative spatial position(s) and the real time spatial orientation(s) of the surgical tool onto at least a portion of the surface contour of the surface section of the minimally invasive surgery cavity comprises depiction data representing an associated depiction of the real time relative spatial position(s) and the real time spatial orientation(s) of the surgical tool onto at least a portion of the surface contour.

Thereby an effective depiction with a concentrated amount of information can be visualised for the user.

In an embodiment the associated depiction of the real time relative spatial position(s) and the real time spatial orientation(s) of the surgical tool onto at least a portion of the surface contour comprises a depiction of the real time relative spatial position(s) onto the surface contour in a direction coordinated with the real time spatial orientation(s) of the surgical tool. The resulting depiction will thereby be a dynamically changing depiction and will thereby show even smaller movements of the surgical tool including tilting movements which will bring very useful information to the user.

Advantageously the orientation data generation means comprises an orientation sensor connected to or integrated with the surgical tool. In an embodiment the surgical tool is part of the depiction system and comprises integrated at least one sensor.

In an embodiment the orientation data generation means comprises an orientation sensor connected to or integrated with the surgical tool. The orientation sensor preferably comprises at least one distance sensor, such as a short range laser based sensor described above. The at least one direction sensor preferably being mounted to emit laser light in distal direction relative to the surgical tool, preferably oriented substantially parallel to the longitudinal direction of the surgical tool.

In an embodiment the position data generation means and the orientation data generation means are at least partly integrated to a combined position data and an orientation data generation means. In practice it will be simpler to have a combined position data and an orientation data generation means.

In this embodiment the position data/position data generation means also comprises orientation data/orientation data generation means.

Preferably the depiction data representing a depiction of the real time relative spatial position(s) of the surgical tool onto the determined 3D surface contour of the surface section of the minimally invasive surgery cavity comprises depiction data encoding a depiction of a dynamic pattern representation, a dynamic scaling of colours representation, a dynamic schematic representation, a dynamic graphical representation and/or a dynamic augmented reality representation.

Advantageously the encoded depiction comprises a non-image-accurate depiction of the surgical tool.

Whereas prior art systems heretofore have been focused on generating 3D vision of a minimally invasive surgery area or a surgical instrument which is an imitation of a real life vision of the minimally invasive surgery area or a surgical instrument the system of the present invention provides a depiction comprising a correlated projection of the real time position and movements and preferably real time orientation of the surgical tool rather than imaging the surgical tool as such. By providing the depiction of the real time relative spatial position(s) of the surgical tool onto the determined 3D surface contour of the surface section of the minimally invasive surgery cavity in form of depiction data encoding a depiction of a dynamic pattern representation, a dynamic scaling of colours representation, a dynamic schematic representation, a dynamic graphical representation and/or a dynamic augmented reality representation, wherein the encoded depiction does not comprise a non-image-accurate depiction of the surgical tool, the resulting depiction can comprise a very high concentration of useful information to the user. For easy decoding of the depiction the user may be trained e.g. as described further later on. Advantageously the depiction also includes sound as exemplified below.

In an embodiment the dynamic scaling of colours comprises a dynamic scaling of shades of one or more colours, such as hue colours.

The term shades are herein used to designate a gradation of a colour with more or less black and/or brightness.

In an embodiment the depiction data comprises data encoding a depiction of a dynamic pattern representation, wherein the dynamic pattern representation comprises a depiction of a virtual pattern resembling an emitted light pattern impinged onto the determined 3D surface contour, wherein the virtual pattern preferably comprises arch shaped and/or ring shaped lines and/or a plurality of angled lines.

Advantageously the dynamic pattern representation comprises a depiction of the virtual pattern onto the determined 3D surface contour, such that the depiction comprises a dynamic modification of the virtual pattern wherein the dynamic modification is correlated to the determined real time spatially position(s) and thereby movements of the surgical tool.

The virtual pattern preferably resembling a light pattern comprising at least spatially dispersed light beam fractions, such as an angular light path surrounding a light dot or a grid of lines, e.g. a crosshatched pattern optionally comprising substantially parallel lines when emitted to a planar surface, and/or one or more angular, such as rectangular shapes e.g.

square shaped, e.g. in an overlapping configuration, in a side by side configuration or concentrically arranged.

In an embodiment the dynamic pattern representation comprises a depiction corresponding to the light pattern reflected and/or scattered from the surface of the surgery site when using the systems and methods disclosed in WO15124159 and/or in co-pending patent application DK PA 2015 70483.

In an embodiment the depiction comprises a depiction of a dynamic scaling of colours representation, wherein the dynamic scaling of colours representation comprises a visual coloured representation of the determined real time spatially position(s) of the surgical tool relative to the determined 3D surface contour wherein the colouring is dynamically modified in correlation to changes of the spatial position and optional orientation caused by the movements of the surgical tool relative to the determined 3D surface contour for example such that the shorter distance between the surgical instrument and the target area the more intensive red and/or less intensive green.

The depiction of a dynamic scaling of colours representation has shown to be very simple to decoding for most users and can comprise a large amount of useful information. Advantageously the depiction systems comprise means (a button or wireless setting means) for setting the colour scaling and brightness. For some users the colour scaling is not sufficient e.g. due to colour blindness and in such situation other depiction are preferred e.g. in combination with the colour scaling representation.

In an embodiment the visual coloured representation comprises a 2D graduated shading.

In an embodiment the depiction comprises a dynamic schematic representation, wherein the dynamic schematic representation comprises a diagrammatic representation of the determined real time spatially position(s) of the surgical tool relative to the determined 3D surface contour wherein the diagrammatic representation is dynamically modified in correlation to changes of the spatial position and optional orientation caused by the movements of the surgical tool relative to the determined 3D surface contour.

In an embodiment the depiction comprises a depiction of a dynamic graphical representation, wherein the dynamic graphical representation comprises a graphical representation of the determined real time spatially position(s) of the surgical tool relative to the determined 3D surface contour wherein the graphical representation is dynamically modified in correlation to changes of the spatial position and optional orientation caused by the movements of the surgical tool relative to the determined 3D surface contour.

In a preferred embodiment the depiction comprises a depiction of a dynamic augmented reality representation, wherein the dynamic augmented reality representation comprises an augmented reality representation of the determined real time spatially position(s) of the surgical tool relative to the determined 3D surface contour wherein the augmented reality representation is dynamically modified in correlation to changes of the spatial position and optional orientation caused by the movements of the surgical tool relative to the determined 3D surface contour.

In an embodiment the augmented reality is a spatial augmented reality (SAR) wherein the display unit comprises one or more digital projectors configured to display the depiction upon receipt of the calculated depiction data e.g. onto a physical object(s), such as onto the patient, such as onto an artificial patient or a head-up display.

Advantageously the depiction comprises a sound depiction, such as a beeping sound where the tone and/or the beep-rate is correlated to the relative distance between the surgical tool and the surface section. The beeping sound may for example intensify as the surgical tool is approaching the surface section e.g. to a point of the surface section distal to the surgical tool in its longitudinal direction.

In an embodiment the depiction comprises a vibration depiction, such as a vibration of the surgical tool, such as of a proximal part of the surgical tool adapted to be sensed by a surgeon holding or being mounted with the surgical tool. The vibration may for example be activated in case the surgical tool is dangerously close to a critical structure of the surface section of the minimally invasive surgery cavity.

In an embodiment the calculated depiction data is configured for being displaced on the display unit, wherein the display unit is selected from a 2D screen, a 3D screen, a projector system (such as an augmented projector system), head-up display, a wearable display unit, such as a head mounted display (e.g. goggles) or any combinations thereof.

In an embodiment the calculated depiction data comprises pixel data for a pixel based display unit, such as a screen, the pixel data preferably comprises red-blue-green pixel data, preferable for displaying high colour or true colour comprising at least 16 bits per pixel (bpp), such as at least 20 bpp.

The pixel data of the depiction data representing a depiction of the real time spatial position(s) of the surgical tool onto the determined 3D surface contour of the surface section of the minimally invasive surgery cavity is preferably dynamically modified in correlation to changes of the spatial position and optional orientation caused by the movements of the surgical tool relative to the determined 3D surface contour.

To obtain a high quality depiction the calculated depiction data advantageously comprises pixel data for a 2D display, such as a 2D display of at least about 1000 pixels, such as at least 10.000 pixels optionally comprising sub-pixels.

In an embodiment the display unit is part of the depiction system, the display unit is preferably selected from a 2D screen, a 3D screen, a projector system (such as an augmented projector system), head-up display, a wearable display unit, such as a head mounted display (e.g. goggles) or any combinations thereof.

To increase the visual perception of the user it is in an embodiment desired that the depiction system comprises a real imaging system configured for generating real imaging data for a real imaging of the at least one surface section of the minimally invasive surgery cavity. The real imaging system is a 2D real imaging system, a 3D real imaging system, a virtual reality real imaging system, an augmented reality real imaging system or any combination thereof.

The term "real imaging" is herein used to mean an imaging where the images show or images the surface section as it is in real life.

The real imaging system may for example be an endoscopic system as it is well known today, e.g. an endoscope for inserting into the minimally invasive surgery cavity and comprising an illuminator for illumination the surface target area and a camera for requiring real images of the target area.

In an embodiment the real imaging system is an augmented reality real imaging system e.g. as describe in "Augmented reality in laparoscopic surgical oncology" by Stéphane Nicolau et al. Surgical Oncology 20 (2011) 189-201 and "An effective visualization technique for depth perception in augmented reality-based surgical navigation"

by Choi Hyunseok et al. The international journal of medical robotics and computer assisted surgery, 2015 May 5. doi: 10.1002/rcs.1657.

Advantageously the real imaging system comprises an image recorder (camera) for acquiring at least one image of the at least one surface of section of the minimally invasive surgery cavity. The image recorder preferably being a part of an endoscope, the image recorder preferably being a videoscope preferably acquiring real time images of the at least one surface section of the minimally invasive surgery cavity.

The image recorder is for example a 2D recorder comprising a 2D array of detectors in form of pixel detectors, preferably the image recorder comprises at least 1000 pixels, such as at least 10.000 pixels, preferably the image recorder is a mega pixel recorder comprising at least 1 mega pixels.

In an embodiment the image recorder is a 3D recorder comprising a 3D array of detectors in form of pixel detectors, preferably the image recorder comprises at least 1000 pixels, such as at least 10.000 pixels, preferably the image recorder is a mega pixel recorder comprising at least 1 mega pixels.

In an embodiment the image recorder or preferably the whole real imaging system constitutes also a part of the 3D surface data generation means for providing the computer system with the three-dimensional (3D) data representing the at least one surface section in 3D space of the minimally invasive surgery cavity.

Preferably the depiction system is configured for transmitting the real imaging data to the display unit for providing a real imaging of the at least one surface section of the minimally invasive surgery cavity, the real imaging preferably comprises displaying the acquired image(s).

By displaying both the real imaging of the at least one surface section of the minimally invasive surgery cavity and the depiction of the real time relative spatial position(s) of the surgical tool onto the surface contour of the surface section of the minimally invasive surgery cavity the visual perception of the user is highly increased. Advantageously depiction system is configured for displaying the real imaging of the at least one surface section of the minimally invasive surgery cavity and the real time correlated depiction of movements of the surgical tool by a common display unit.

Advantageously the depiction system is configured for displaying the real imaging of the at least one surface section of the minimally invasive surgery cavity and onto the real imaging of the at least one surface section of the minimally invasive surgery cavity to display the depiction of the real time relative spatial position(s) of the surgical tool onto the surface contour of the surface section of the minimally invasive surgery cavity.

Preferably the depiction of the real time relative spatial position(s) of the surgical tool onto the surface contour of the surface section of the minimally invasive surgery cavity is projected onto the real imaging of the at least one surface section of the minimally invasive surgery cavity, the depiction of the real time relative spatial position(s) of the surgical tool onto the surface contour of the surface section of the minimally invasive surgery cavity is preferably at least partly transparent for the real imaging of the at least one surface section of the minimally invasive surgery cavity. Thereby the user can on the same display se both the real imaging of the at least one surface section of the minimally invasive surgery cavity and onto the real imaging of the at least one surface section of the minimally invasive surgery cavity to display the depiction of the real time relative spatial position(s) of the surgical tool onto the surface contour of the surface section of the minimally invasive surgery cavity in a correlated way, which further increase the visual perception.

In an embodiment the depiction system comprises a robot controller for controlling a robot which preferably form part of the depiction system. The robot and the robot controller may in an embodiment be as described in US 2009/0248041. The robot controller is in data connection with or is integrated with the computer system. In the following the robot controller is describe as being in data communication with the computer system but it should be interpreted such that the computer controller as well can be an integrated part of the computer system.

The robot controller being configured for receiving at least a part of the obtained or generated data preferably comprising said 3D surface data and said real time spatial position data and preferably said real time orientation data. Optionally the robot controller is also configured for receiving derived data—i.e. data derived from the 3D surface data and said real time spatial position data and preferably said real time orientation data—such as the depiction data. The robot controller is preferably configured for controlling the robot for handling the surgical tool for performing a minimally invasive surgery procedure.

In an embodiment the robot controller is configured for acquiring the required data from the computer system respective data from said computer system.

Advantageously the robot controller is configured for receiving instructions from a supervisor, such as an assisting surgeon and/or a robot operator. The controller is preferably configured for receiving instructions from the supervisor by data input via a digital user interface and/or by oral instruction.

The robot controller is preferably configured to modify movements of said surgical tool in response to the supervisor instructions. The supervisor instruction may for example instruct the robot to move the surgical tool a cm to the right or a few mm distally in longitudinal direction of the surgical tool or etc.

In an embodiment the depiction system is configured for simultaneously, via the robot controller, controlling the robot for handling the surgical tool for performing a minimally invasive surgery procedure and for transmitting said depiction data to the display unit. The depiction will in this embodiment comprise a real time correlated depiction of said movements of said surgical tool by said robot. The supervisor may keep the robot under observation during its performing of the minimally invasive surgery via the depiction and thereby control that the robot is operation sufficiently accurate or as explained, the supervisor may correct the robot by feeding instructions to the robot controller.

The computer system preferably comprises a memory and is advantageously configured for storing performance data sets, where each performance data set comprises performance data associated with a minimally invasive procedure, such as for minimally invasive procedure that has been performed using the depiction system. The performance data preferably comprises at least the position data for the minimally invasive procedure, and preferably at least one of the 3D data, the orientation data, the depiction data for the minimally invasive procedure or any combination thereof. Preferably the performance data set comprises all the data acquired during a minimally invasive surgery procedure. In an embodiment the performance data set further comprises calculated data including the depiction date.

In an embodiment the performance data comprises at least one of the position data, the 3D data, the orientation data or the depiction data for the minimally invasive procedure.

In an embodiment the computer system is programmed to analyse the respective performance data set and to transmit a feedback evaluation(s) of the respective minimally invasive procedures to a display means.

In an embodiment the computer system is programmed to analyse the respective performance data set and preferably the computer system is configured to transmit a feedback evaluation(s) of the respective minimally invasive procedures to a display means, such as the display unit and/or a printer.

Thereby a user—i.e. a surgeon or a person under training for becoming a surgeon—can in a very simple way receive feedback and he can evaluate his improvement. Advantageously the computer system is configured to transmit a feedback evaluation(s) upon a request. Each performance data set preferably has a unique code such that the respective performance data sets can be retrieved for displaying of the depiction of the real time relative spatial position(s) of the surgical tool e.g. for the surgeon or for training purpose of other surgeons.

In an embodiment the computer system is programmed to determine an improved performance data set relative to a selected performance set, and to transmit at least a part of the data, such as depiction data of the improved performance data set to a display means, such as the display unit and/or a printer.

Preferably the computer is programmed to compare the improved performance data set relative to the selected performance set and the selected performance set to determine data differences and to transmit the data differences to a display means, such as the display unit and/or a printer.

Thereby the user can compare his performance with a superior performance data set e.g. a calculated performance data set and he can retrieve information about what can be improved, where he uses superfluous movements etc.

In an embodiment the computer system is programmed to determine difference in performance data, categorizing the data and store the categorized data for machine learning purposes.

In an embodiment the computer system is programmed to transmit selected data of the one or more performance data set to a display means, such as the display unit and/or a printer, preferably upon request from a user.

Thereby the respective performance data sets can be retrieved for displaying of the depiction of the real time relative spatial position(s) of the surgical tool e.g. for use in education.

In an embodiment the depiction system is configured for operating in a training mode. The surgical tool is a training tool, which may or may not resemble a real surgical tool.

The depiction system when operating in its training mode is configured for determine training depiction data representing a training depiction of the real time relative spatial position(s) of the training tool onto at least a portion of the surface contour of the surface section of the minimally invasive surgery cavity, and for transmitting the training depiction data to the display unit for real time correlated depiction of movements of the training tool.

When the depiction system is in its training mode the minimally invasive surgery cavity surface section may for example be an artificial surface section and in this embodiment the training tool may advantageously be an artificial tool.

In an embodiment the minimally invasive surgery cavity surface section when the depiction system is in its training mode is an actual minimally invasive surgery cavity. In this embodiment the training tool is a real surgical tool. In principle the surgeons is constantly in training for improving their technique in order to perform a minimally invasive surgery as optimal as possibly—e.g. using the least movements of the surgical tool possibly and/or performing the minimally invasive surgery as fast as possible.

In an embodiment the position data generation means being configured for obtaining real time spatial position data of at least a part of the training tool and for transmitting the obtained spatial position data to the computer system, the computer system being programmed for calculating the training depiction data representing the training depiction of the real time relative spatial position(s) of the training tool onto at least a portion of the surface contour of the surface section of the minimally invasive surgery cavity, and for transmitting the training depiction data to the display unit for real time correlated depiction of movements of the training tool.

The computer system is advantageously configured for transmitting the training depiction data and associated performance depiction data of stored performance data set for the same or a corresponding minimally invasive surgery cavity to the display unit for real time correlated depiction of movements of the training tool. Preferably the transmission of the training depiction data and associated performance depiction data are timely associated.

Thereby a user during training can benchmark against an earlier performed minimally invasive surgery procedures or calculated procedures or his own earlier procedures.

In an embodiment the computer system is configured for transmitting the training depiction data and associated performance depiction data of stored performance data set for the same or a corresponding minimally invasive surgery cavity for performing a benchmarking of the performance depiction data relative to said training depiction data.

In an embodiment the performance depiction data set is transmitted to the display unit in a speed of about real-time speed.

In an embodiment the performance depiction data set is transmitted to the display unit in a speed which is less than real-time speed.

Thereby a person under training can perform the minimally invasive surgery procedure at a slower pace for training purpose and he can step-by-step increase the pace to reach the real time speed or even faster if desired for training purpose.

In an embodiment the computer system is configured for receiving supervisor input e.g. from a user or a training database, to determine supervisor depiction data based on the supervisor input and transmitting the supervisor depiction data to the display unit, preferably the computer is configured for acquiring the supervisor input from a training database. The supervisor input may be input representing selected positions and movements of the training tool.

In an embodiment the superviser is a robot in data communication with the computer system.

Advantageously the computer system is configured for transmitting the training depiction data and the associated performance depiction data and/or the supervisor depiction data to the display unit to be displayed separately, such as in a side by side configuration. Thereby the person under training, such as a surgeon aiming to improve his skill can be trained to position the training tool in a selected position or moving the training tool in a select way as instructed by the supervisor input. The person under training can try to move the training tool such that the training depiction follows associated performance and/or the supervisor depiction.

In an embodiment the supervisor is another surgeon observing and advising a surgeon during a minimally invasive surgery procedure. In an embodiment there are for example two surgeons operating together, where one is handling the surgical tool and the other one is acting as supervisor making suggestions for positioning and movements of the surgical tool and visa verse. It should be understood that the display unit may be in form of two or more sub unit.

All features of the inventions including ranges and preferred ranges can be combined in various ways within the scope of the invention, unless there are specific reasons not to combine such features.

BRIEF DESCRIPTION OF EXAMPLES

Preferred embodiments of the invention will be further described with reference to the drawings.

FIG. 3 is an example of a 3D database system—classification scheme.

FIG. 4 is an example of a 3D database system—3D data set scheme.

FIG. 7 is a schematic transverse cross sectional view of a minimally invasive surgery cavity and a number of sensors.

Figure 15:
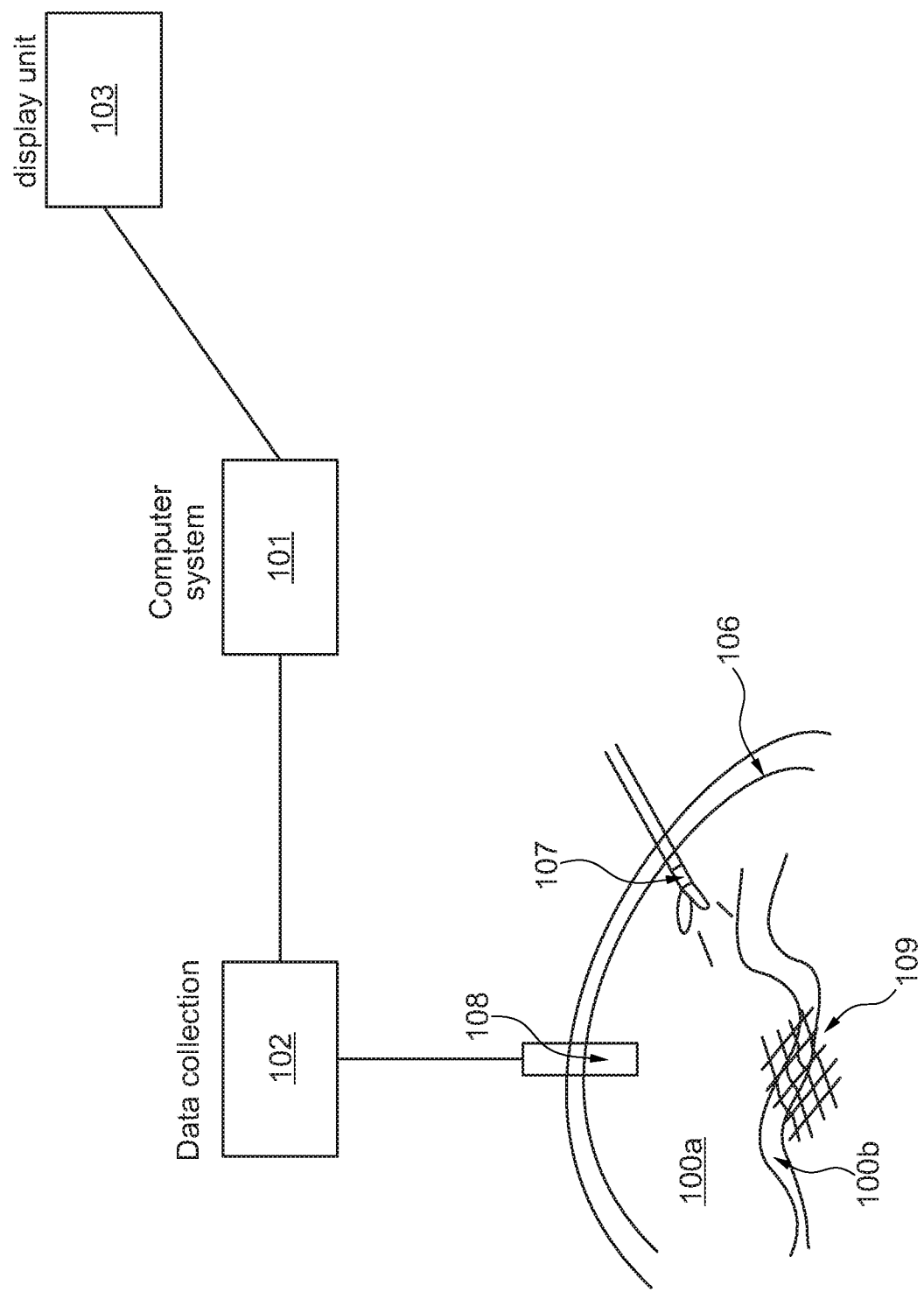

FIG. 15 is an illustration of an example of a depiction system of the invention wherein the surgical tool comprising a pattern emitting projector emitted onto the surface section of the minimally invasive surgery and the 3D surface data generation means and/or the position data generation means and/or the orientation data generation means comprises a data collection system in data connection with or integrated with the computer system, and where the data collection system comprises an optical recorder.

Figure 16:
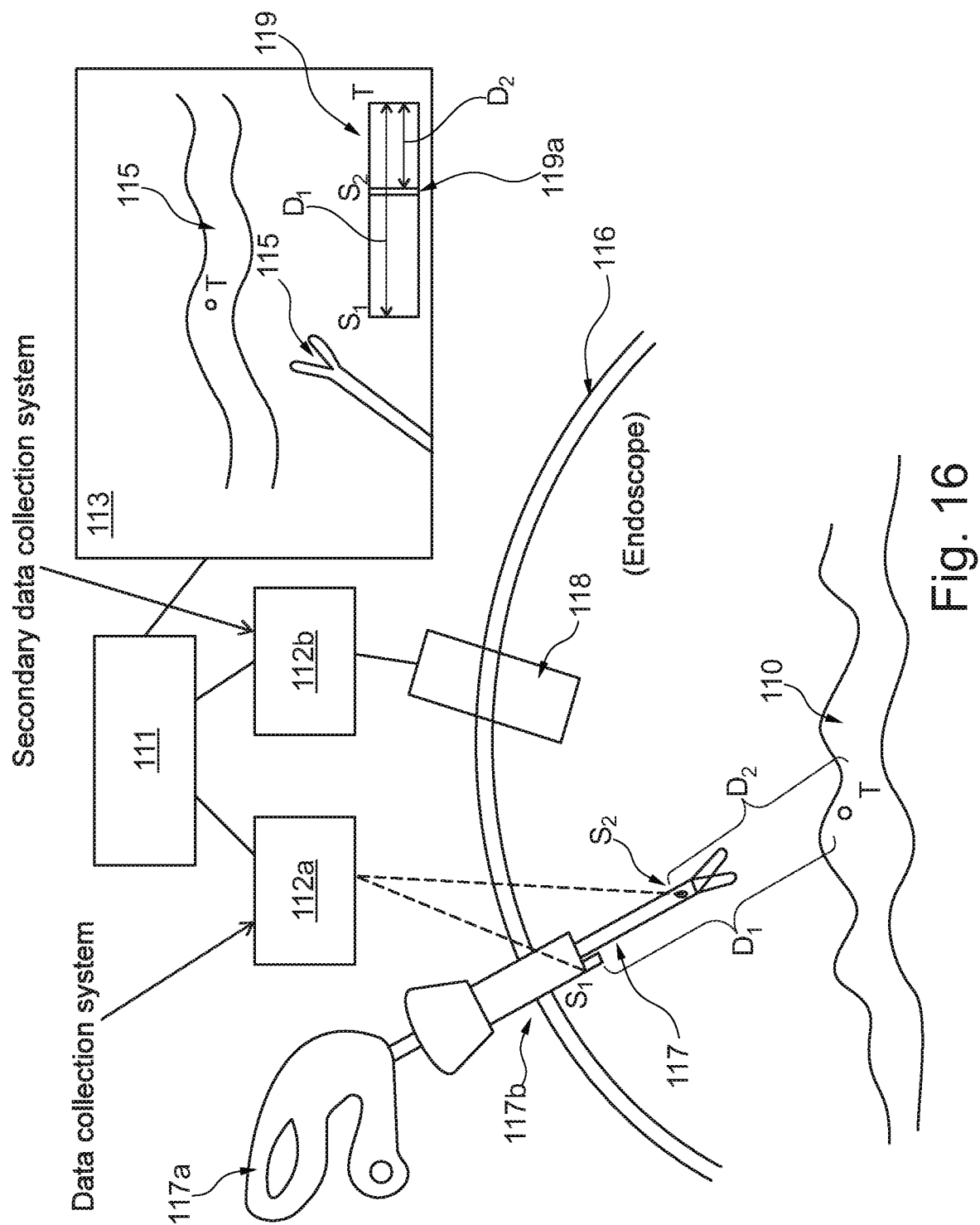

FIG. 16 is an illustration of an example of a depiction system of the invention wherein the surgical tool as well as the cannula/trocar each comprises a sensor, the depiction system comprises a data collection system for collecting data from the sensors, a data collection system for collecting data from a reader and is further configured for generating a graphical depiction besides a real image of the relevant surface section of the minimally invasive surgery.

Figure 17:
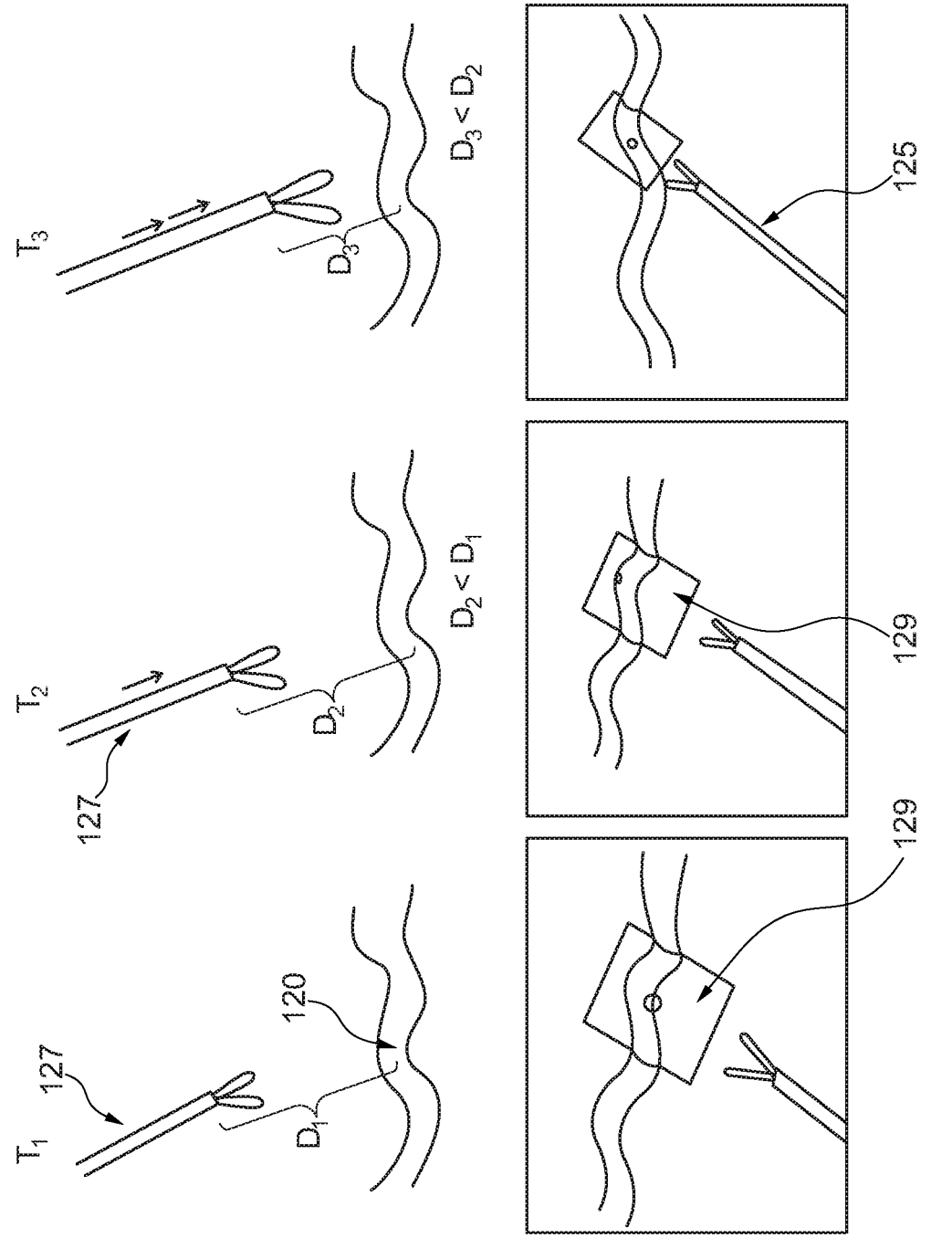

FIG. 17 is an illustration of an example of real time correlated depictions of movements of a surgical tool at 3 consecutive points in time, wherein the surgical tool is positioned with different distance to the surface section in longitudinal distal direction to the surgical tool.

Figure 18:
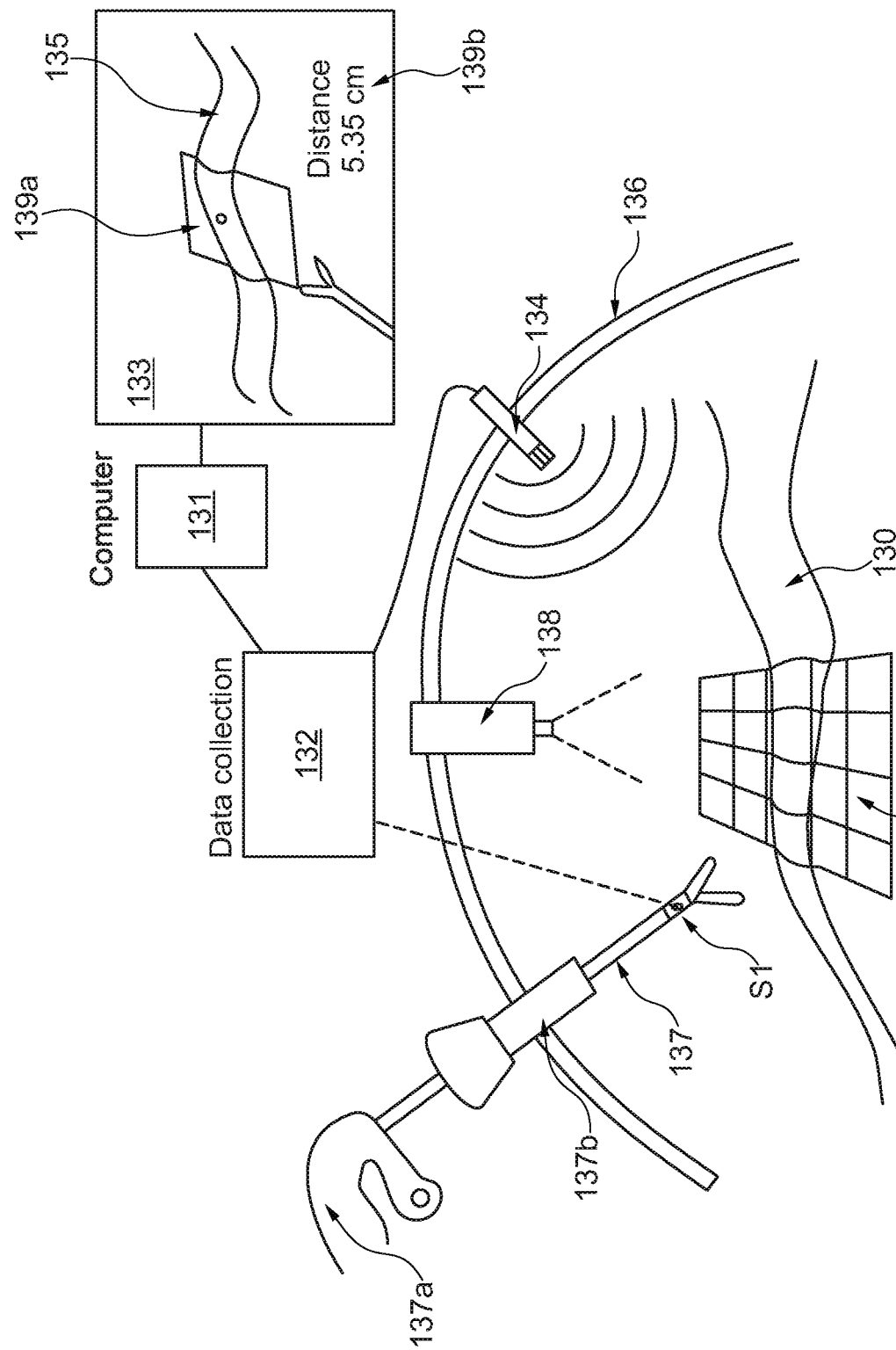

FIG. 18 is an illustration of an example of a depiction system of the invention comprising a data collection system for collecting data from a sensor mounted onto the surgical tool, an optical recorder as well as an acoustic sensor, such as an ultrasound sensor, a wherein the depiction system is configured for generating a depiction onto a real image.

Figure 19:
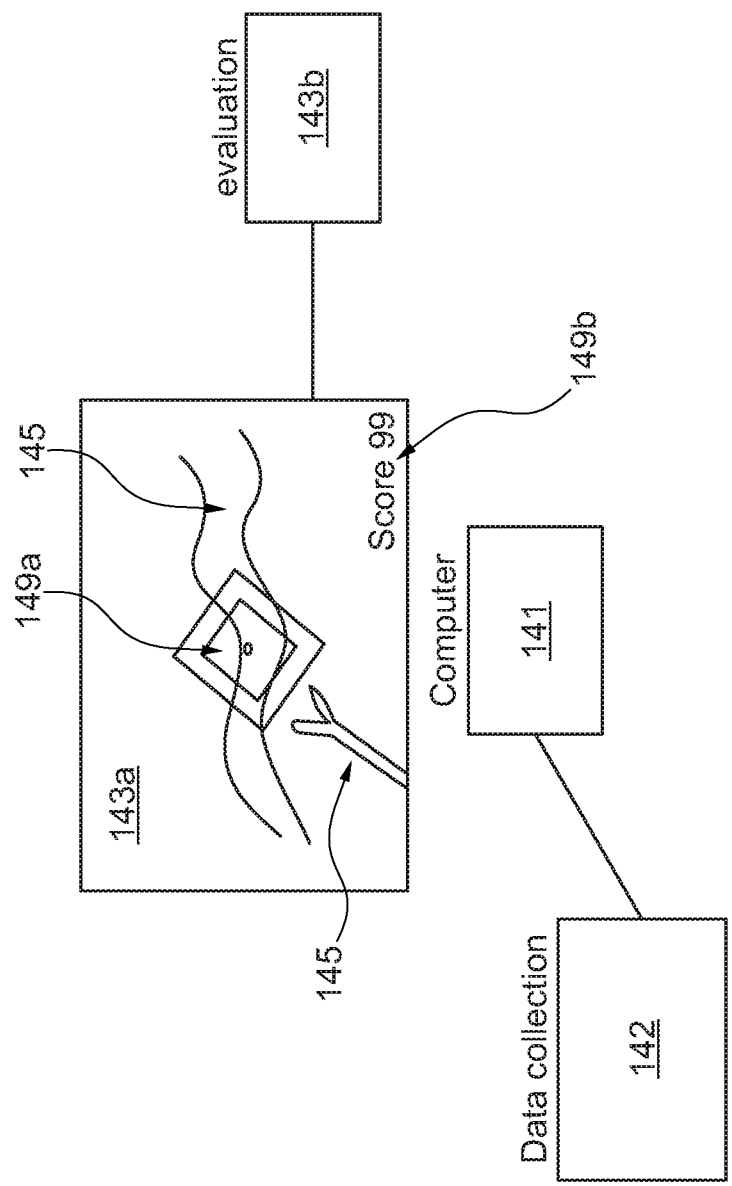

FIG. 19 is an illustration of an example of a depiction system of the invention comprising a data collection system for collecting data from not shown sensors. The computer system stores a plurality of performance data sets and is configured to benchmark against a selected performance data set and to evaluate a minimally invasive surgery procedure by a user. The computer system is in digital connection with an additional display unit such as a smart phone or a printer for transmitting the evaluation.

Figure 20:
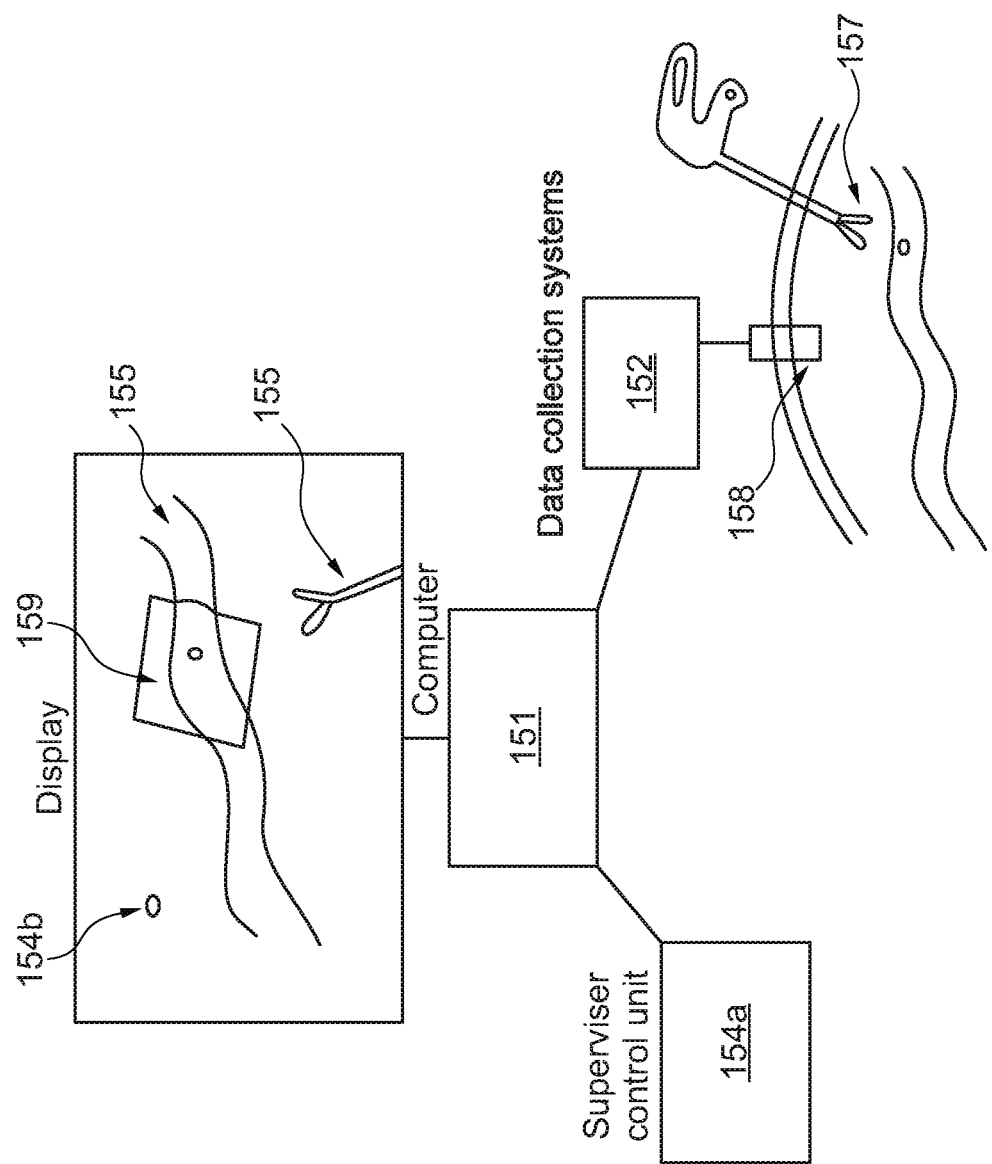

FIG. 20 is an illustration of an example of a depiction system of the invention comprising a data collection system for collecting data from a recorder and other not shown sensors. The computer system is in data connection with a supervisor control unit for receiving input. The depiction is displayed onto a display unit together with a real image and a supervisor input.

FIG. 21 is an illustration of an example of a depiction system of the invention comprising a data collection system for collecting data from a recorder and other not shown sensors. The computer system is in data connection with a robot controller for transmitting 3D surface data, real time spatial position data and real time orientation data to the robot controller. The robot controller is configured for controlling a robot for handling the surgical tool for performing a minimally invasive surgery procedure and the depiction system display the depiction, which comprises a real time correlated depiction of movements of the surgical tool by the robot.

The figures are schematic and are not drawn to scale and may be simplified for clarity. Throughout, the same reference numerals are used for identical or corresponding parts.

Figure 1:
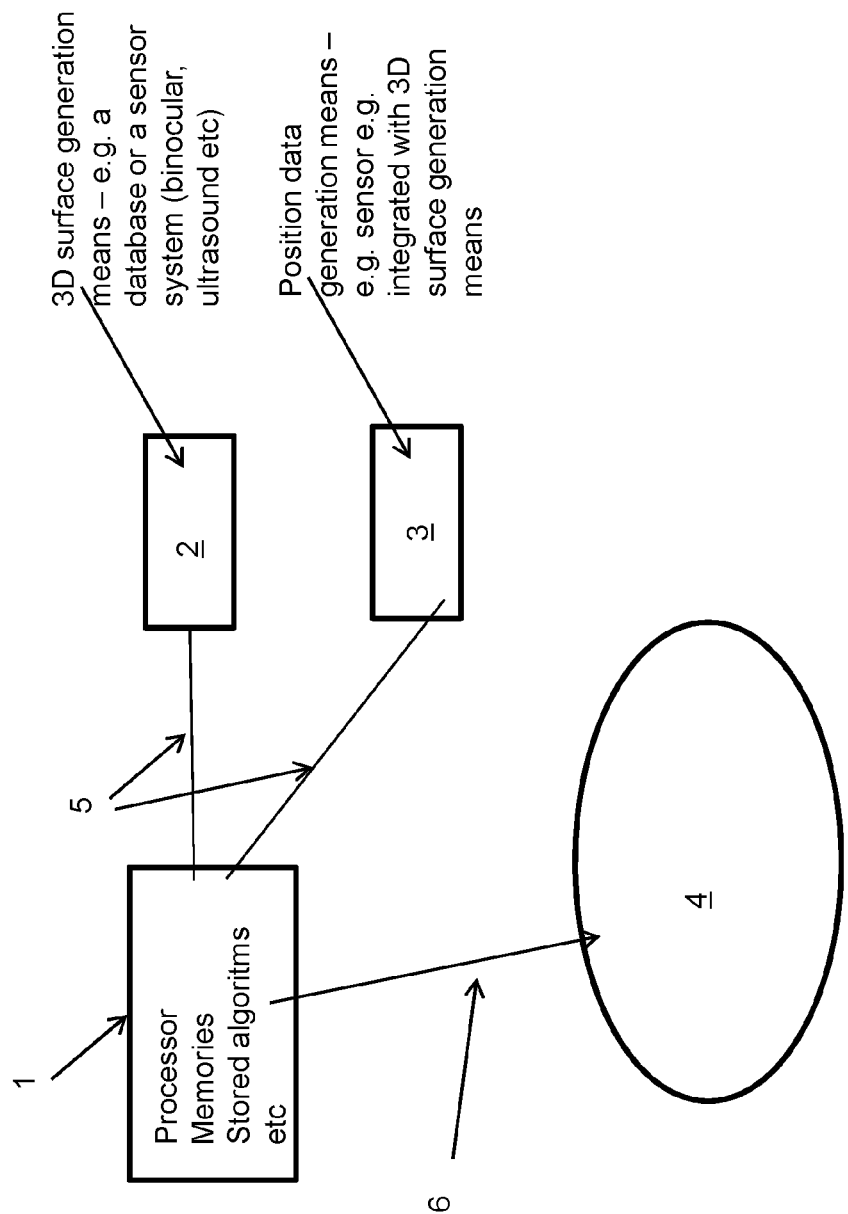
FIG. 1 is a schematic view of an embodiment of a depiction system of the invention.

The depiction system illustrated in FIG. 1 comprises a computer system 1, 3D surface data generation means 2 and position data generation means 3 in data connection with the computer system 1, e.g. as illustrated with wires 5 or wireless for feeding 3D surface data and real time position data to the computer system 1. The computer system 1 is here illustrated as one unit, but as explained the computer system could comprise two or more units in data communication depiction system of the invention.

The computer system 1 is programmed for
determining a 3D surface contour of at least a part of the target area of an not shown surface section of the minimally invasive surgery cavity using the 3D data,
determining real time spatially position(s) of a not shown surgical tool relative to at least a part of the target area of the at least one surface section using the spatial position data and the surface position data,
calculating depiction data representing a depiction of the real time relative spatial position(s) of the surgical tool onto at least a portion of the surface contour of the surface section of the minimally invasive surgery cavity, and for
transmitting the depiction data to the display unit 4 for real time correlated depiction of movements of the surgical tool.

The display unit can be as described above.

Figure 2:
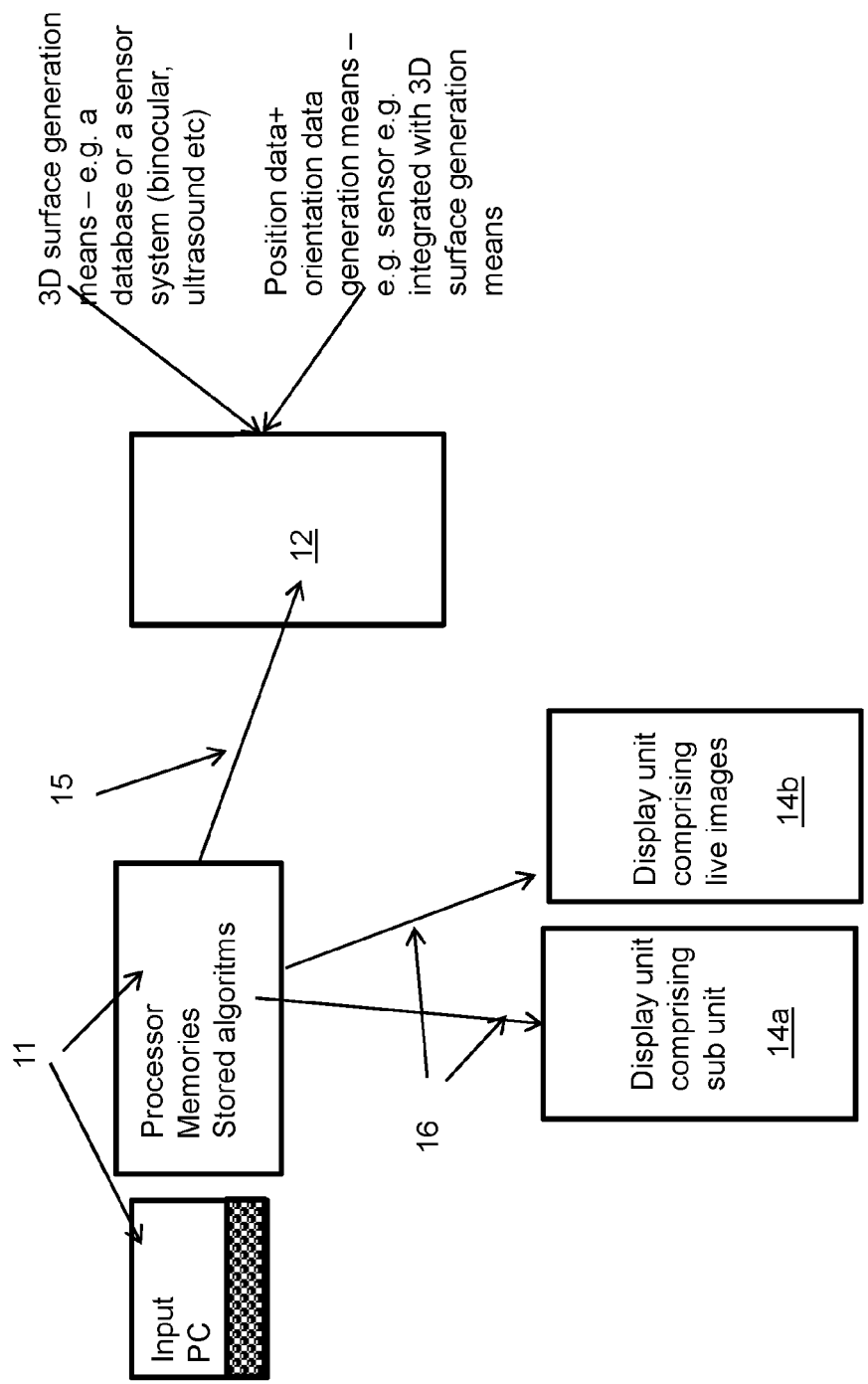
FIG. 2 is a schematic view of another embodiment of a depiction system of the invention.

The depiction system illustrated in FIG. 2 also comprises a computer system 11 e.g. as the computer system of FIG. 1. The depiction system of FIG. 2 differs from the depiction system of FIG. 1 in that it comprises a combined 3D surface data generation means and position data generation means 12 and in that it comprises a display unit in form of two display sub unit 14a, 14b. Advantageously the real time correlated depiction of movements of the surgical tool is displayed on one of the sub unit 14a and real images e.g. live images and/or benchmarking depiction is displayed on the other sub unit 14b.

FIG. 3 illustrates a classification scheme which may be comprised in a 3D database system. As indicated each classification has a unique code, linking each classification to one or more 3D data sets. Each classification set is classified in accordance with a classification set comprising a number of patient characteristics as indicated in the scheme of FIG. 3 and comprises for example age, gender, weight, height, body circumferential dimension(s) or any combinations thereof. The selected characteristics depend largely on the type of minimally invasive surgery cavity in question.

FIG. 4 illustrates a scheme of 3D data sets which may be comprised in a 3D database system, wherein each 3D data set is associated to to a patient characteristic as indicated with the unique codes, corresponding to the unique codes of FIG. 3.

Figure 5:
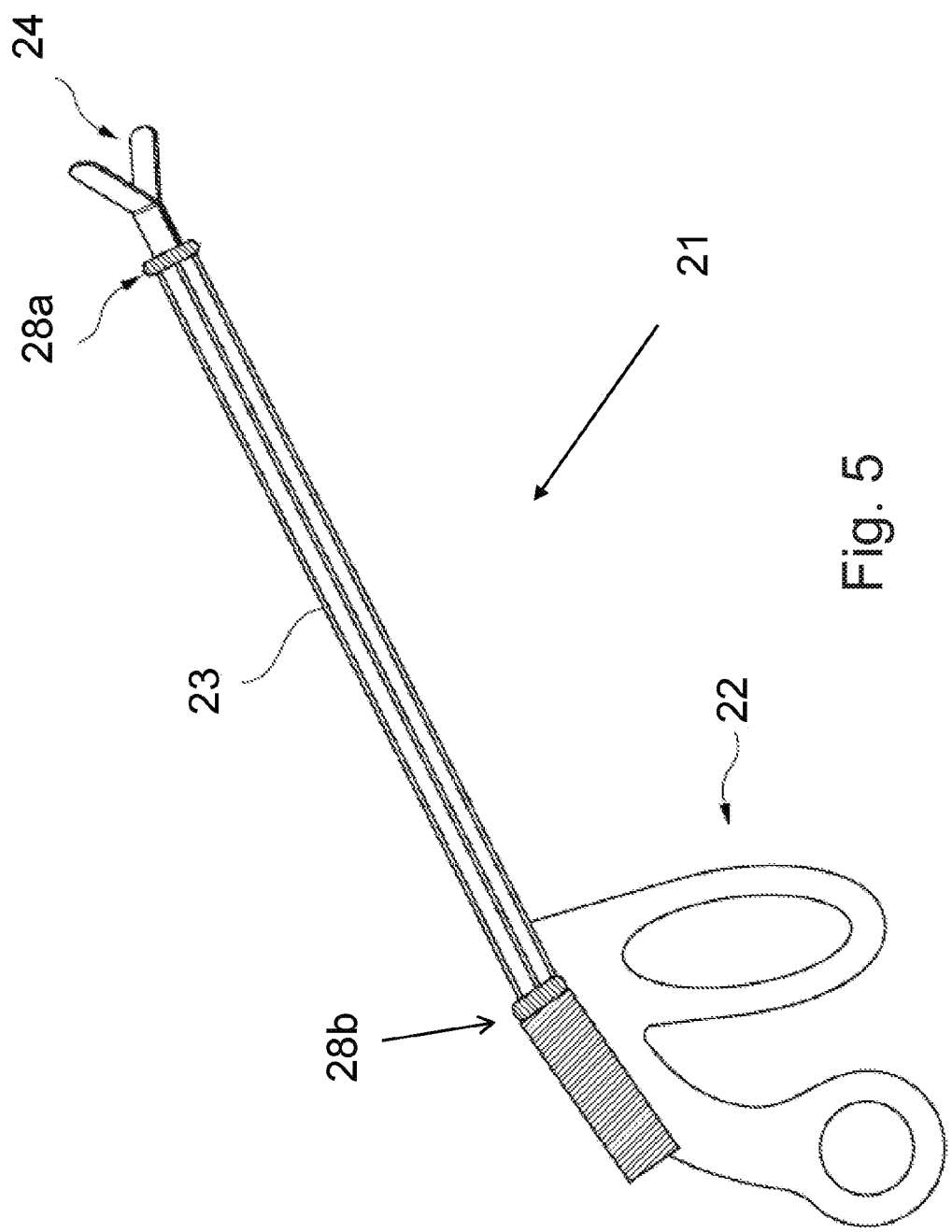
FIG. 5 is a schematic side view of a surgical instrument comprising a surgical tool.

The surgical instrument shown in FIG. 5 is a laparoscopic instrument. It should be understood that in the invention other surgical instrument with surgical tool could as well be applied.

The surgical instrument has a handle portion 22 and a body tool portion 23 with a surgical tool portion 24 in the present case forceps. The surgical tool portion 24 and the part of the body portion 23 adapted to be inserted into the minimally invasive surgery cavity is referred to as the surgical tool. In other words the surgical instrument 21 comprises the surgical tool 23, 24 and the handle 22. The body portion 23 interconnect the handle portion 22 which is arranged at the proximal end of the surgical instrument and the surgical tool portion 24, which is arranged at the distal end of the surgical instrument. The body portion 23 is arranged in the distal/proximal direction, which is also referred to as the longitudinal direction of the surgical tool 23, 24.

In another embodiment the surgical tool portion 24 may be another surgical tool portion e.g. a grasper, a suture grasper, a stapler, a dissector, scissors, a suction instrument, a clamp instrument, an electrode, a curette, ablators, scalpels, a needle holder, a biopsy and retractor instrument or a combination thereof.

The surgeon operate the surgical instrument 21 by holding the handle portion 22 and can in this way control the surgical tool and by pressing or manipulating the handle portion the forceps can be controlled.

The surgical instrument 21 further comprises a first sensor 28a, such a sensor as described above, mounted to the surgical tool and a second sensor 28b mounted at the handle. The sensor may be linked to the not shown data collecting system of the computer system e.g. by wire (for example optical fiber(s) or wireless e.g. blue tooth. The two sensors may provide both real time position data as well as real time orientation data.

In an alternative embodiment the surgical instrument may comprise a pattern generating arrangement. The surgical tool with a handle may for example be in form of a surgical instrument assembly as described in WO15124159. The reflected/scattered pattern may thus be collected by a reader and transmitted to a data collecting system of the computer system to provide a part of the 3D surface data, which may preferably also be real time 3D data and the real time position data and preferably also real time orientation data.

Figure 6:
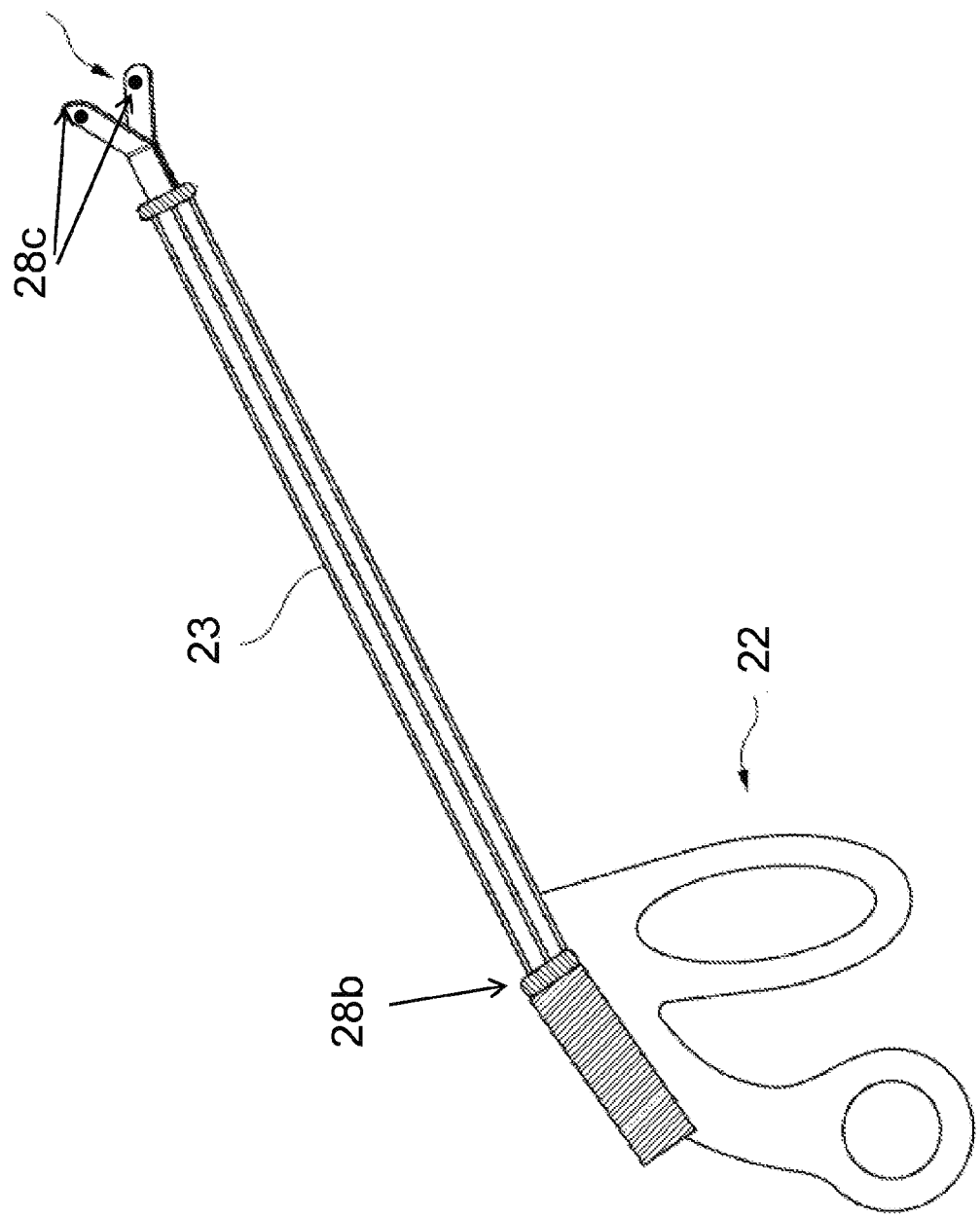
FIG. 6 is a schematic side view of another surgical instrument comprising a surgical tool.

FIG. 6 illustrates a variation of the surgical instrument of FIG. 5, where the pair of sensors 28c is positioned on the graspers of the forceps of the surgical tool portion 24 of the surgical tool. Thereby the movements of the graspers may be monitored as well and at the same time the sensors 28c on the graspers may be used to determine the real time position data and the real time orientation data.

FIG. 7 illustrates a minimally invasive surgery cavity 31—here the abdominal cavity of a patient 36. The minimally invasive surgery cavity 31 is seen in a transverse cross sectional view. The anatomic plans of a human patient are indicated in the image 30 and the minimally invasive surgery cavity 31 is seen in the transverso plan from the top vertical view.

The patient 36 is positioned on an operation table 33 with his back 34 against the table 33 and his front 35 upwards. The minimally invasive surgery cavity is blown up by injecting a gas into the cavity through a not shown incision and the surface is indicated with reference 32. As illustrated the minimally invasive surgery cavity surface 32 may be very uneven and with large curved projections and recesses.

A number of sensors 38a are positioned onto the operation table. Only 4 sensors 38a are shown, but preferably at least 4 sensors 38a are positioned in a rectangular configuration on the operation to define an X-Y-Z plan and optionally with additional sensors.

Further a number of sensors 38b are mounted to the patient e.g. within the minimally invasive surgery cavity 31 as shown.

The sensors 38a, 38b may e.g. be as described above.

Figure 8:
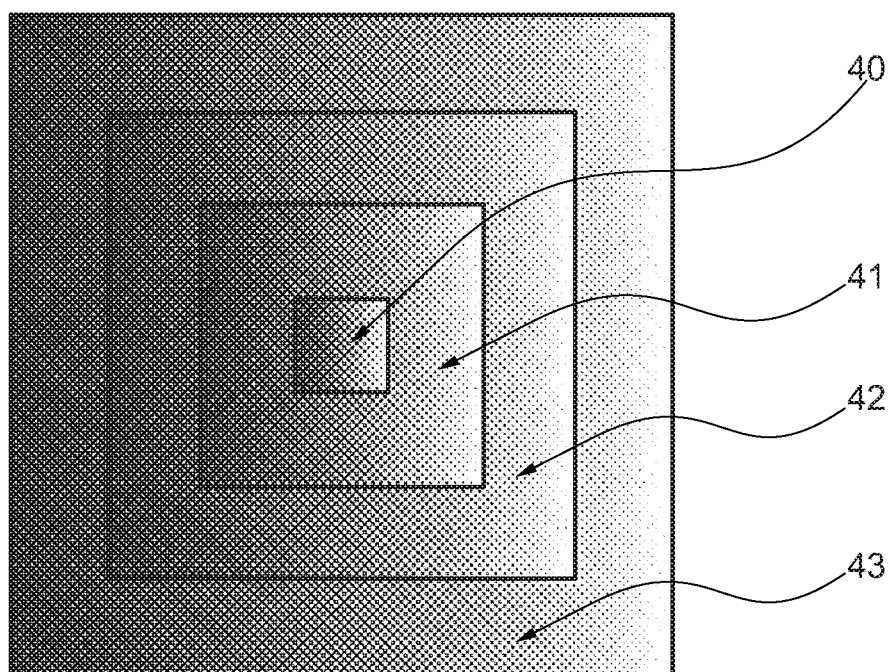
FIG. 8 is an illustration of an example of a real time correlated depiction of movements of a surgical tool, wherein the depiction comprises a dynamic changing of color scales correlated with movement of the not shown surgical tool.

An example of a real time correlated depiction of movements of a surgical tool is illustrated in FIG. 8. The depiction comprises a number of squared sections 41, 42, 43 concentrically arranged to surround a central area 40. The dynamic depiction may advantageously change in a correlation with movement of a not shown surgical tool, e.g. by changing the width of the respective squared sections 41, 42, 43 individually from each other, by changing the corner angles of the respective squared sections 41, 42, 43 individually from each other, by changing the color and/or color pattern of the respective squared sections 41, 42, 43 individually from each other, by changing the size and/or shape of the central area 40 or by any combinations thereof. For example the size of the central area 40 may indicate the distance between the surgical tool and the minimally invasive surgery cavity surface section e.g. seen in longitudinal distal direction from the surgical tool. The color or color variations along the square shape of one or more of the respective squared sections 41, 42, 43 may indicate the orientation of the tool, and the width and/or the corner angles of the respective squared sections 41, 42, 43 may indicate the contour of the cavity surface section. When the surgical tool is moved the depiction will be changing in a way which is correlated with movement of the surgical tool.

Figure 9:
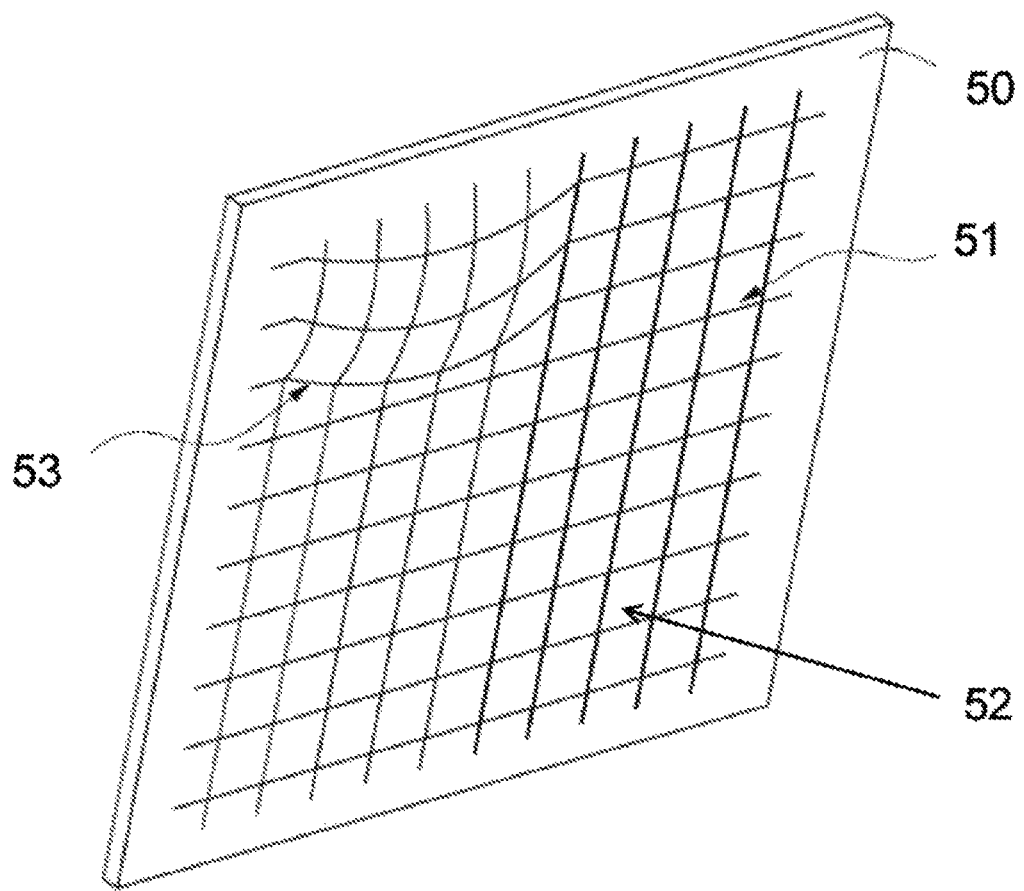
FIG. 9 is an illustration of an example of a real time correlated depiction of movements of a surgical tool, wherein the depiction comprises a dynamic changing of pattern correlated with movement of the not shown surgical tool.

Another example of a real time correlated depiction of movements of a surgical too is illustrated in FIG. 9. The depiction is displayed on a displayer 50 in form of a flat screen. The depiction comprises a dynamic changing of pattern correlated with movement of the not shown surgical tool. The pattern is a crosshatched pattern 51 comprising a grid of lines which when the surgical tool is far from the surface section has parallel, straight and crossed lines, whereas when the surgical tool is within a selected distance from the surface section the lines are bending as indicated with the reference 53 in dependence on the contour of the surface. At the same time the distance between parallel lines may reflect the distance between the surgical tool and the minimally invasive surgery cavity surface section e.g. seen in longitudinal distal direction from the surgical tool. Further the angles between the crossing lines may indicate the orientation and angulation of the surgical tool. When the surgical tool is moved the depiction will be changing in way which is correlated with movement of the surgical tool.

Figure 10:
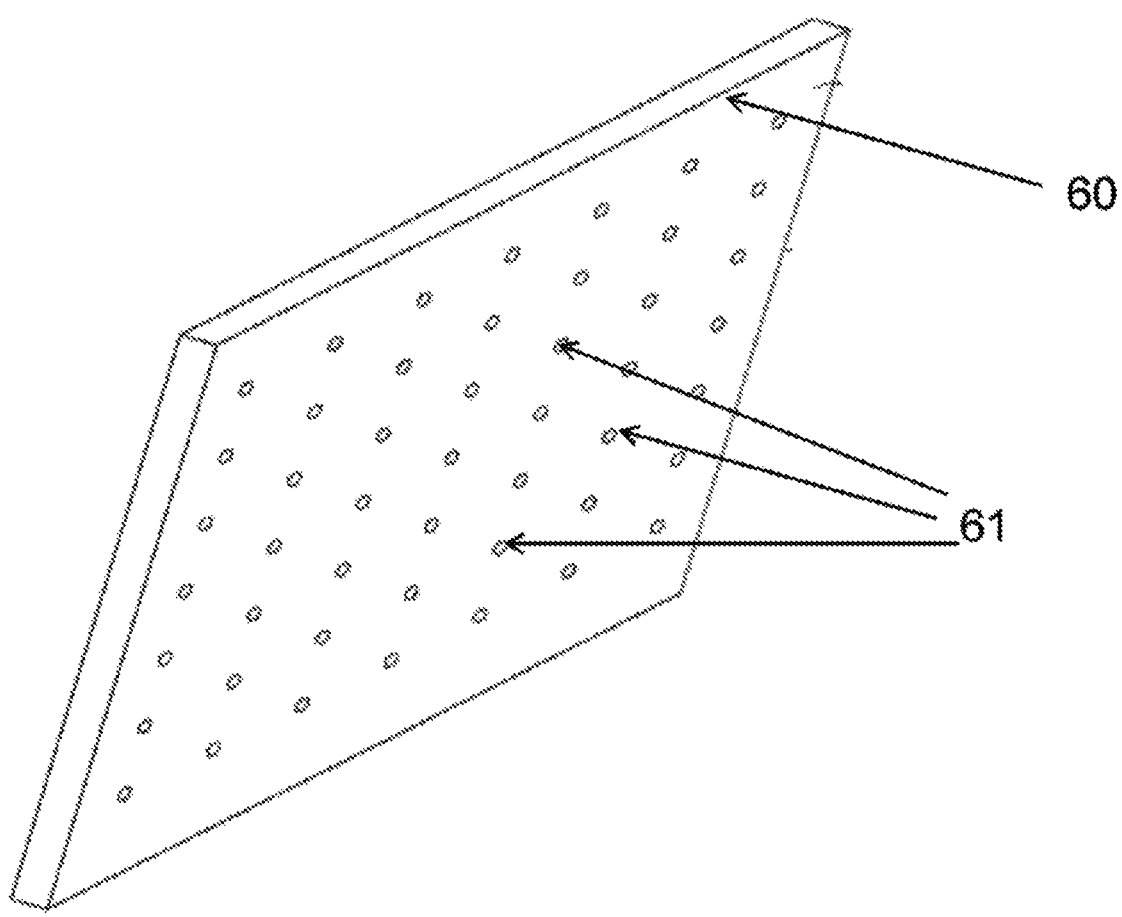
FIG. 10 is an illustration of an example of a real time correlated depiction of movements of a surgical tool, wherein the depiction comprises a dynamic changing of light dots correlated with movement of the not shown surgical tool.

A further example of a real time correlated depiction of movements of a surgical tool is illustrated in FIG. 10. The depiction is displayed on a displayer 60 in form of a flat screen. The depiction comprises a dynamic changing of light dots 61 correlated with movement of the not shown surgical tool. The light dots 61 are illustrated in their home position where the surgical tool is far from the surface section and the light pattern is very regular. When the surgical tool is within a selected distance from the surface section the position of the light dots are changing in dependence on the contour of the surface. At the same time the size of the light dots may reflect the distance between the surgical tool and the minimally invasive surgery cavity surface section e.g. seen in longitudinal distal direction from the surgical tool. Further the number of light dots or the relative sizes of light dots may indicate the orientation and angulation of the surgical tool. When the surgical tool is moved the depiction will be changing in way which is correlated with movement of the surgical tool.

Figure 11:
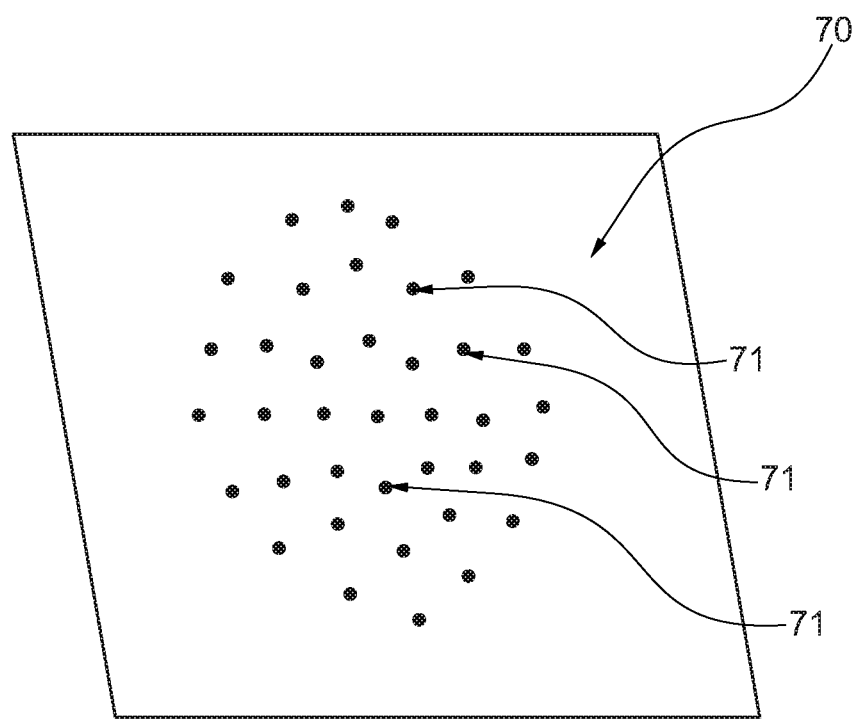
FIG. 11 is an illustration of an example of a real time correlated depiction of movements of a surgical tool, wherein the depiction comprises a dynamic changing of color dots correlated with movement of the not shown surgical tool.

A variation of the depiction of FIG. 10 is illustrated in FIG. 11. Here the light dots 71 are arranged in another home configuration and the dots 71 may further have varying colours e.g. in dependence of the distance to the target area.

Figure 12:
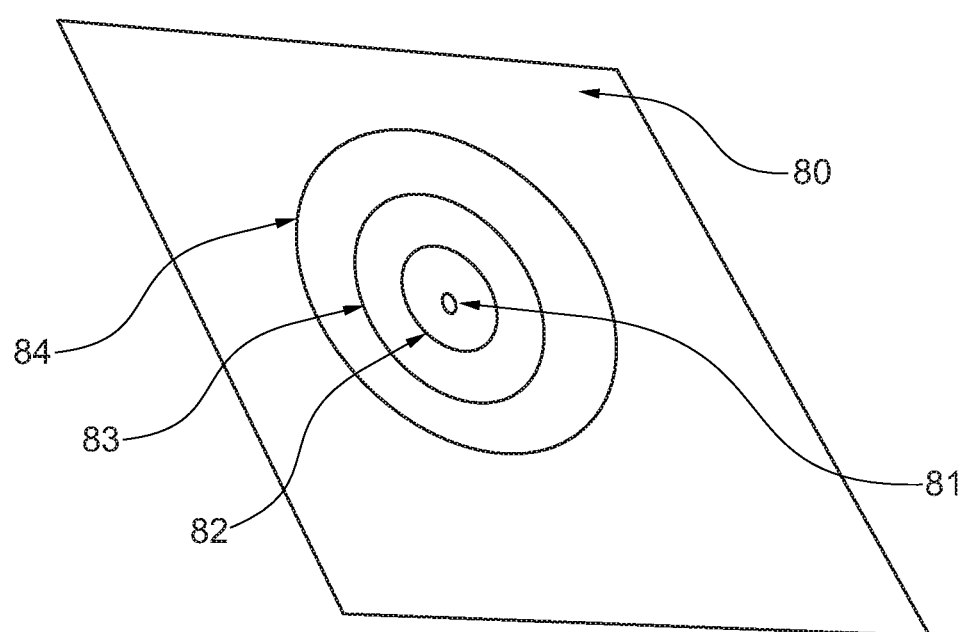
FIG. 12 is an illustration of an example of a real time correlated depiction of movements of a surgical tool, wherein the depiction comprises a dynamic changing of rings correlated with movement of the not shown surgical tool.

The time correlated depiction of movements of a surgical tool illustrated in FIG. 12 comprises a dynamic changing of rings 81, 82, 83, 84 correlated with movement of the not shown surgical tool. The rings 81, 82, 83, 84 are concentrically arranged and may vary in size, in shape, in line thickness, in line color, in individual distances and or in other in way to indicate surface contour, distances, orientation and other information which may be relevant for the user e.g. as described above.

Figure 13:
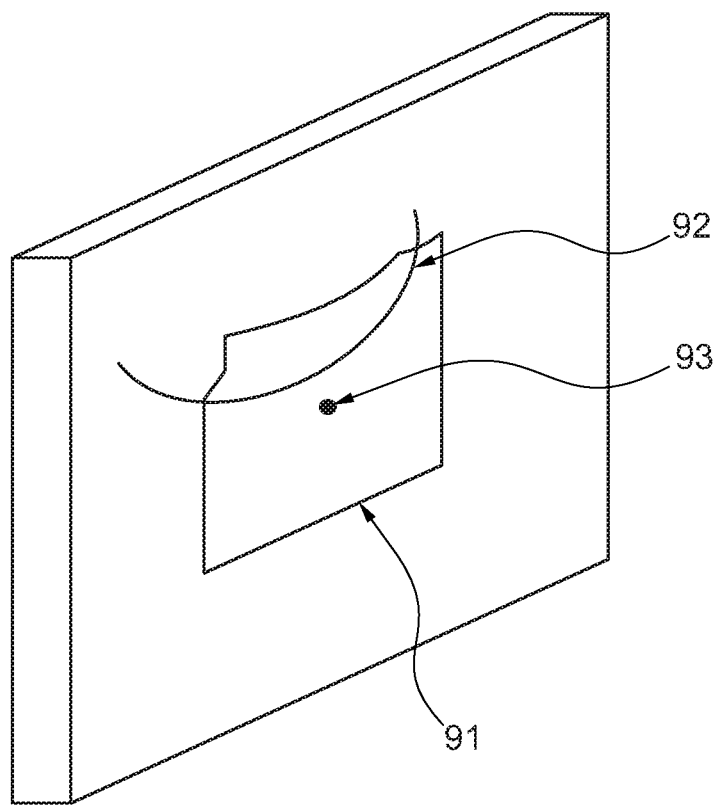
FIG. 13 is an illustration of an example of a real time correlated depiction of movements of a surgical tool, wherein the depiction comprises a dynamic changing of a perimeter and a bulge shaped marking correlated with movement of the not shown surgical tool and where an additional supervisor instruction is depicted.

The time correlated depiction of movements of a surgical tool illustrated in FIG. 13 comprises a dynamic changing of a perimeter 91 and a bulge shaped marking 92 correlated with movement of the not shown surgical tool. The shape, size, line thickness and/or color of the perimeter 91 may e.g. change in dependence of the contour of the surface section the distance between the surgical tool and the surface section and/or the orientation of the surgical tool and the bulge shaped marking 92 may e.g. change in dependence of the distance between the surgical tool and the target area and optionally of the orientation of the surgical tool relative to the target area. The dot 93 indicates a marker for the longitudinal direction of the not shown surgical tool.

Figure 14:
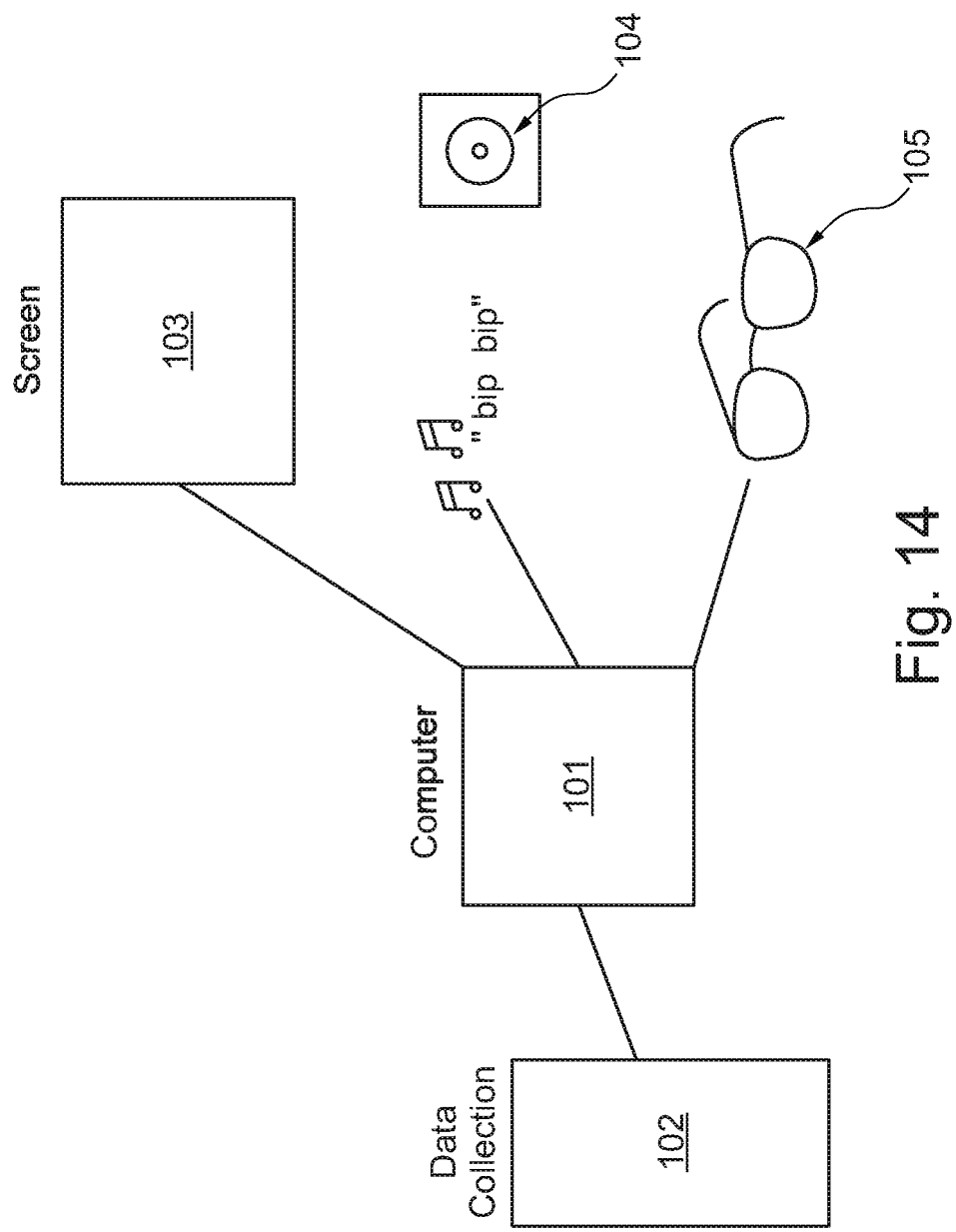
FIG. 14 is an illustration of an example of a depiction system of the invention wherein the depiction comprises sound and/or the display comprises a goggle based display.

FIG. 14 illustrates at least a part of a depiction system comprising a computer system where a computer 101 and a data collection system 102 of the depiction system are shown. The data collection system 102 is configured for collecting the various data comprising at least 3D surface data and real time position data. The collected data is transmitted to the computer 101 for calculating depiction data and the depiction data is transmitted to one or more display units comprising a screen 103, a loud speaker 104 for displaying a sound depiction e.g. a beep—beep sound as explained above and/or goggles 105 for displaying on a wearable display unit.

As it can be understood the display and the depiction may take many different forms.

The depiction system of FIG. 15 is a variation of the depiction system of FIG. 14 where only the screen display 103 is indicated. The depiction system comprises an endoscope 108 and a surgical instrument with a not shown handle e.g. forming part of or integrated with a robot arm and a surgical tool 107 configured for emitting a light pattern.

The surgical tool may have a handle for example be in form of a surgical instrument assembly as described in WO15124159.

The surgical tool is inserted through a not shown incision through the skin layer 106 of a patient and into the minimally invasive surgery cavity 100*a*. The light pattern is emitted towards the relevant surface section 100*b* and the light pattern 109 is impinging on and a part is reflected and/or scattered from the surface section 100*b* of the minimally invasive surgery cavity 100*a*. The endoscope comprises an optical recorder for recording the reflected and/or scattered light pattern 109, and the collected data which advantageously includes 3D surface data (in real time), real time position data and real time orientation date is transmitted by wire or wireless to the data collection system 102. In a variation thereof the optical recorder 108 is not a part of an endoscope but inserted through the skin layer 106 at another place than the site of the endoscope entry. In another variation the optical recorder 108 is fixed to or integrated with the surgical tool.

The depiction system illustrated in FIG. 16 comprises a computer system where a computer 111 and a data collection system of the depiction system are shown. The data collection systems 112*a* is configured for collecting the various data comprising at least 3D surface data and real time position data and to transmit the data to the computer 111 for calculating depiction data and the depiction data is transmitted to one or more display units comprising a screen 113.

In the illustrated embodiment the depiction system comprises an endoscope 118 and a surgical instrument with a handle 117*a* and a surgical tool 117. The surgical tool may further emit a light pattern as described in FIG. 15.

The endoscope 118 comprises a recorder for recording real images of the surface section and the surgical tool. The real images are collected in a secondary data collection system 112*b* of the computer system and transmitted to the computer from where they are transmitted for displaying on the screen 113 such that the real images 115 are timely associated with the depiction 119.

In the shown FIG. 16 the surgical instrument is inserted through an incision in the skin layer 116 of a patient via a cannula/trocar 117*b* which generates an access port for the surgical tool 117. A sensor S2 is mounted to the surgical tool 117 and another sensor S1 is mounted to the cannula 117*b*. A target area T is marked at the surface section 110 for illustrative purposes.

The computer has information about the position of this target area T e.g. via the images recorded by the recorder 118 of by other means. The respective sensors S1 and S2 are advantageously distance sensors configured for determining the respective distances D1 and D2 to the target area T and preferably also the respective position of the sensors S1, S2 relative to the target area to thereby determine the orientation of the surgical tool 117. Optionally, the longitudinal direction of the surgical tool 117 is marked/depicted by a dot at target area T.

The real images 115 and the depiction are displayed on the display 113 besides each other. The target area T may also be shown on the real image 115. The depiction 119 is a graphical depiction showing the distance D1 between sensor S1 and the target area T as well as the distance D2 between sensor S2 and the target area T. e.g. by a bar indicator 199*a* that is moved in horizontal direction.

FIG. 17 illustrates a real time correlated depictions of movements of a surgical tool 127 at 3 consecutive points in time T1, T2, T3, wherein the surgical tool is positioned with different distance D1, D2, D3 to the surface section 120 e.g. a target area of the surface section in longitudinal distal direction to the surgical tool. As it can be seen the depiction 129 on the real image 125 at the time T1 where the distance D1 is relatively large, is accordingly relatively large. At the time T2 the distance D2 is smaller than D1 and the depiction 129 is accordingly smaller. At the time T3 the distance D3 is smaller than D2 and the depiction 129 is accordingly even smaller. The displayed size of the real image 125 is kept substantially constant.

The depiction system illustrated in FIG. 18 comprises a computer system where a computer 131 and a data collection system 132 of the depiction system are shown. The data collection systems 132 is configured for collecting the various data comprising at least 3D surface data and real time position data and to transmit the data to the computer 131 for calculating depiction data and the depiction data is transmitted to one or more display units comprising a screen 133. The depiction system further comprises an endoscope 138, an acoustic sensor 134, such as an ultrasound sensor, and a surgical instrument with a handle 137*a* and a surgical tool 137. The surgical tool may further emit a light pattern as described in FIG. 15.

The endoscope 138 comprises an arrangement for emitting a light pattern and a recorder for recording real images of the surface section and the surgical tool 137. The real images are collected in the data collection system 132 of the computer system and transmitted to the computer 131 from where they are transmitted for displaying on the screen 133 such that the real images 135 are timely associated with the depiction 139.

In the shown FIG. 18, the surgical instrument is inserted through an incision in the skin layer 136 of a patient via a cannula 137*b* which generates an access port for the surgical tool 137. A sensor S1 is mounted to the surgical tool 137 for collection real time position data and transmitting the data to the data collection system. The endoscope 138 is inserted through another incision in the skin layer 136 of the patient. The endoscope is emitting a stationary pattern such as a crosshatched pattern, which is impinging onto and at least partly reflected/scattered from the surface section 130 of the cavity, thereby revealing the surface contour of the surface section which is recorded both in form of 3D surface data and in form of real images by the recorder of the endoscope 138. The acoustic sensor 134 is inserted through a further incision through the skin layer 136 of the patient for recording additional 3D surface data. All the recorded data and images are transmitted to the data collecting system 132. The data and images are transmitted to the computer 131 for calculating depiction data and the depiction data and the images are in a timely associate fashion transmitted to the display 133 for being displayed, where the real images 135 are displayed and a part of the depiction 139*a* are displayed on top of the real images 135. The part of the depiction 139*a* displayed on top of the real images 135 are advantageously at least partly transparent for the real images 135. The depiction also comprises a graphical depiction part 139*b* e.g. in form of a distance indication displayed beside the real images for example indicating the distance between the surgical tool and a target area.

The depiction system illustrated in FIG. 19 comprises a data collection system 142 and a computer 141 of a depiction system. The data collection systems 142 is configured for collecting the various data from not shown 3D surface data generation means, position data generation means and optionally other means as described above, where the data comprises at least 3D surface data and real time position data. The data collection systems 142 is further configured for collecting real images as described above and for transmitting the data and images to the computer 141 for calculating depiction data and the depiction data and the images are in a timely associate fashion transmitted to the display 143*a*, where at least a part of the depiction 149*a* are displayed on top of the real images 145. The part of the depiction 149*a* displayed on top of the real images 145 are advantageously at least partly transparent for the real images 145. The computer stores a number of performance data sets as explained above and is programmed to analyse and optionally benchmark the performance of a user relatively to one or more stored performance data set—e.g. generated by the same user for determine his improvement. In the example in FIG. 19 the computer system has transmitted the user score 149*b* for being displayed. The depiction system is further digital connected to a printer, other display unit and/or a smart phone 143*b* for printing or displaying a full evaluation of a user performance of a minimally invasive surgery procedure. The full evaluation may include both timely benchmarking and spatially surgical tool movement benchmarking as well as any other benchmarking.

The depiction system illustrated in FIG. 20 comprises a data collection system 152 and a computer 151 of a depiction system. The data collection systems 152 is configured for collecting the various data from various 3D surface data generation means, position data generation means and optionally other means e.g. from an endoscope recorder 158 and/or sensor on a surgical tool 157 as described above, where the data comprises at least 3D surface data and real time position data. The data collection systems 152 is further configured for collecting real images as described above and for transmitting the data and images to the computer 151 for calculating depiction data and the depiction data and the images are in a timely associate fashion transmitted to the display 153, where at least a part of the depiction 159 are displayed on top of the real images 155. The part of the depiction 159 displayed on top of the real images 155 are advantageously at least partly transparent for the real images 155.

The depiction system further comprises a supervisor control unit 154a in communication with or comprised in its computer system. The supervisor control unit comprises a digital user (supervisor) interface and/or a sound recorder for recording supervisor input, such as supervisor instructions. The supervisor input data are transmitted via the computer 151 to the display 153 for being displayed as a supervisor depiction 154b.

The depiction system illustrated in FIG. 21 a data collection system 162 and a computer 161 of a depiction system. The data collection systems 162 is configured for collecting the various data from various 3D surface data generation means, position data generation means and optionally other means e.g. as explained herein e.g. below. The data comprises at least 3D surface data and real time position data. The data collection systems 162 may further be configured for collecting real images as described above and for transmitting the data and images to the computer 161 for calculating depiction data and the depiction data and the images are in a timely associate fashion transmitted to the display 163.

In the illustrated embodiment the data generation means comprises an endoscope 168 comprising an arrangement for emitting a light pattern and a recorder for recording reflected/scattered light from the pattern and optionally for recording real images of the surface section and the surgical tool 167. In a variation of the shown embodiment the arrangement for emitting a light pattern and a recorder for recording reflected/scattered light from the pattern is not a part of an endoscope 168 but inserted through the skin layer 166 at another place than the site of the endoscope entry. The surgical tool 167 of the depiction system is also configured for emitting a light pattern.

The surgical tool with a handle may for example be in form of a surgical instrument assembly as described in WO15124159. The handle and/or the whole surgical tool may for example be a part of a robotic arm.

The endoscope 168 is inserted through an incision in the skin layer 166 of the patient. The endoscope is emitting a stationary pattern such as a crosshatched pattern 168a, which is impinging onto and at least partly reflected/scattered from the surface section of the cavity, thereby revealing the surface contour of the surface section which is recorded both in form of 3D surface data and preferably also in form of real images by the recorder of the endoscope 168.

The surgical tool 167 is inserted through another incision (or same incision) through the skin layer 166 of the patient and into the minimally invasive surgery cavity. The light pattern is emitted towards the relevant surface section and the light pattern 167a is impinging on and at least partly reflected and/or scattered from the surface section of the minimally invasive surgery cavity. As the surgical tool 167 is moved the pattern 167a emitted from the surgical tool 167 becomes a dynamic pattern 167a upon the stationary pattern 168a from the endoscope 168. As the reflected and/or scattered light is recorded by the recorder of the endoscope 168 large amounts of 3D surface data, real time position data as well as real time orientation data is obtained and transmitted to the data collection system 162. The movements of the dynamic pattern may be for example be related to the stationary pattern and the relevant 3D, position and orientation data may be determined using trigonometric calculation methods.

The depiction system further comprises a robot controller 160. The computer 161 is in data connection with the robot controller 160 for transmitting at lease a part of the collected data including 3D surface data, real time spatial position data and real time orientation data to the robot controller 160. The robot controller 160 is configured for controlling a not shown robot for handling the surgical tool for performing a minimally invasive surgery procedure and the depiction system is configured for displaying the depiction, which comprises a real time correlated depiction of movements of the surgical tool by the robot. Thereby a supervisor e.g. an operator can keep the robot under observation during its performing of the minimally invasive surgery via the displayed depiction and thereby control that the robot is operation sufficiently accurate or as explained, the supervisor may correct the robot by feeding instructions to the robot controller e.g. via a supervisor control unit as shown in FIG. 20.

The figures are schematic and are not drawn to scale and may be simplified for clarity. Throughout, the same reference numerals are used for identical or corresponding parts.

What is claimed is:

1. A depiction system for generating a real time correlated depiction of movements of a surgical tool, the system comprising
    a computer system,
    3D surface data generation means adapted for providing the computer system with three-dimensional (3D) data representing at least one surface section in 3D space of a minimally invasive surgery cavity, wherein said surface section comprises a target area, and
    position data generation means adapted for obtaining real time spatial position data of at least a part of the surgical tool and for transmitting said obtained spatial position data to said computer system,
    wherein at least one of said 3D surface data generation means and said position data generation means comprises surface position data generation means adapted for providing surface position data of at least said target area, said computer system being programmed for
    determining a 3D surface contour of at least a part of said target area of said surface section of said minimally invasive surgery cavity using said 3D data,
    determining real time spatial positions of said surgical tool relative to at least a part of said target area of said at least one surface section using said spatial position data and said surface position data,
    calculating depiction data representing a depiction of said real time relative spatial positions of said surgical tool onto at least a portion of said surface contour of said surface section of said minimally invasive surgery cavity, and for
    transmitting said depiction data to a display unit for real time correlated depiction of movements of said surgical tool, wherein the depiction data is graphically overlaid on an image of said target area and presented on the display unit in a graphical depiction, the graphical depiction overlaid on the image of said target area and comprising a bounded region that is configured to contract when the tool is advanced toward the target area and configured to expand when the tool is retracted away from the target area, wherein a displayed size of the image remains substantially constant when the tool is advanced or retracted.

2. The depiction system of claim 1, wherein the 3D surface data generation means comprises a 3D database system, the 3D database system comprising at least one 3D data set for at least one surface section of each of a plurality of classified minimally invasive surgery cavities, wherein each 3D data set is associated to said respective surface section(s) of at least one of said classified minimally invasive surgery cavities, and wherein said computer is configured for acquiring at least one 3D data set for at least one surface section of a classified minimally invasive surgery cavity.

3. The depiction system of claim 2, wherein one or more of said 3D data sets comprises estimated 3D data, calculated 3D data, measured 3D data or any combination thereof, said 3D data sets each is associated to a patient characteristic.

4. The depiction system of claim 1, wherein the 3D surface data generation means comprises a 3D surface sensor system for determining at least a part of said 3D data for at least said surface section of said minimally invasive surgery cavity and transmitting means for transmitting said determined for 3D data to said computer.

5. The depiction system of claim 4, wherein the sensor system for determining at least a part of said 3D data for at least said surface section of said minimally invasive surgery cavity is configured for generating at least one of pre-operative data or intra-operative data.

6. The depiction system of claim 4, wherein the 3D surface sensor system comprises at least one local reference sensor.

7. The depiction system of claim 4, wherein the 3D surface sensor system comprises a 3D optical sensor system comprising at least one optical source and at least one optical reader and wherein the at least one optical source is configured for emitting an optical tracking light pattern which pattern when impinged onto and reflected and/or scattered from the surface reveal the contour of the surface to thereby provide 3D data to be recorded by the optical reader.

8. The depiction system of claim 7, wherein said at least one of said optical pattern emitting source and said recorder being positioned on an endoscope.

9. The depiction system of claim 7, wherein the optical source is adapted for emitting a dynamic optical pattern onto at least a part of the surface section.

10. The depiction system of claim 7, wherein the depiction system comprises both a stationary and a dynamic optical pattern source, said computer system being configured for generating at least a part of said 3D data and said real time position data simultaneously.

11. The depiction system of claim 1, wherein the position data generation means for obtaining real time spatial position data of at least a part of the surgical tool comprises a position sensor system, said position sensor system comprises a 3D optical sensor, an acoustic sensor, a magnetic sensor, an electric sensor, an accelerometer, a gyroscope, a gravimeter, an inertial navigation system, a local positioning system or any combinations thereof.

12. The depiction system of claim 11, wherein said depiction system comprises a robot controller in data communication with said position sensor for receiving position data and for using said position data for controlling a robot for handling said surgical tool.

13. The depiction system of claim 11, wherein said position sensor system is configured for obtaining real time spatial position data of the surgical tool and for transmitting said obtained spatial position data to said computer system in the form of real time spatial position data in an X-Y-Z.

14. The depiction system of claim 11, wherein said real time spatial position data comprises position data correlated to said 3D data representing at least one surface section in 3D space and said real time spatial position data comprises a distance from the surgical tool of said at least one part of said surgical tool to said target area of said surface section.

15. The depiction system of claim 14, wherein said real time spatial position data comprises position data comprises a distance from said surgical tool to a critical structure.

16. The depiction system of claim 15, wherein said orientation data generation means comprises an orientation sensor.

17. The depiction system of claim 15, wherein said depiction comprises a sound depiction.

18. The depiction system of claim 15, wherein said depiction comprises a vibration depiction, comprising a vibration of the surgical tool.

19. The depiction system of claim 1, wherein said system further comprises orientation data generation means for obtaining real time spatial orientation data of at least a part of the surgical tool and for transmitting said obtained spatial orientation data to said computer system, said computer system being programmed for
determining real time spatially orientation(s) of said surgical tool using said spatial orientation data,
calculating depiction data representing a depiction of said real time spatial orientation(s) of said surgical tool onto at least a portion of said surface contour of said surface section of said minimally invasive surgery cavity, and for
transmitting said depiction data to said display unit for real time correlated depiction of movements of said surgical tool.

20. The depiction system of claim 19, wherein said depiction data representing a depiction of said real time relative spatial position(s) and said real time spatial orientation(s) of said surgical tool onto at least a portion of said surface contour of said surface section of said minimally invasive surgery cavity comprises depiction data representing an associated depiction of said real time relative spatial position(s) and said real time spatial orientation(s) of said surgical tool onto at least a portion of said surface contour.

21. The depiction system of claim 1, wherein said depiction data representing a depiction of said real time relative spatial position(s) of said surgical tool onto said determined 3D surface contour of said surface section of said minimally invasive surgery cavity comprises depiction data encoding a depiction of a dynamic pattern representation, a dynamic scaling of colors representation, a dynamic schematic representation, a dynamic graphical representation and/or a dynamic augmented reality representation.

22. The depiction system of claim 21, wherein said encoded depiction comprises a non-image-accurate depiction of the surgical tool.

23. The depiction system of claim 21, wherein said depiction data comprises data encoding a depiction of a dynamic pattern representation, wherein the dynamic pattern representation comprises a depiction of a virtual pattern resembling an emitted light pattern impinged onto the determined 3D surface contour, wherein the virtual pattern preferably comprises arch shaped and/or ring shaped lines and/or a plurality of angled lines.

24. The depiction system of claim 23, wherein the depiction system is configured for displaying said real imaging of the at least one surface section of the minimally invasive surgery cavity and onto said real imaging to display said depiction of said real time relative spatial position(s) of said surgical tool onto said surface contour of said surface section of said minimally invasive surgery cavity.

25. The depiction system of claim 21, wherein the dynamic pattern representation comprises a depiction of said virtual pattern onto the determined 3D surface contour, to provide that the depiction comprises a dynamic modification of the virtual pattern wherein the dynamic modification is correlated to the determined real time spatially position(s) of said surgical tool.

26. The depiction system of claim 21, wherein said depiction comprises a depiction of a dynamic augmented reality representation, wherein the dynamic augmented reality representation comprises an augmented reality representation of the determined real time spatially position(s) of said surgical tool relative to said determined 3D surface contour wherein the augmented reality representation is dynamically modified in correlation to changes of the spatial position and orientation caused by the movements of the surgical tool relative to said determined 3D surface contour.

27. The depiction system of claim 1, wherein said depiction system comprises a real imaging system configured for generating real imaging data for a real imaging of said at least one surface section of said minimally invasive surgery cavity, said real imaging system comprises a 2D real imaging system, a 3D real imaging system, a virtual reality real imaging system or an augmented reality real imaging system.

28. The depiction system of claim 1, wherein said depiction system comprises a robot controller in data connection with or integrated with said computer system, said robot controller being configured for receiving said respective data and for controlling a robot for handling said surgical tool for performing a minimally invasive surgery procedure.

29. The depiction system of claim 28, wherein depiction system being configured for, controlling said robot for handling said surgical tool for performing a minimally invasive surgery procedure and for transmitting said depiction data to said display unit, wherein said depiction comprises a real time correlated depiction of said movements of said surgical tool by said robot.

30. The depiction system of claim 1, wherein said computer system comprises a memory and is configured for storing performance data sets, each performance data set comprises performance data associated with a minimally invasive procedure.

31. The depiction system of claim 30, wherein said performance data comprises at least one of said position data, said 3D data, said orientation data or said depiction data for said minimally invasive procedure.

32. The depiction system of claim 30, wherein said computer system is programmed to analyze said respective performance data set and to transmit a feedback evaluation(s) of said respective minimally invasive procedures to a display means.

33. The depiction system of claim 30, wherein said computer system is programmed to determine difference in performance data, categorizing the data and store it for machine learning purposes.

34. The depiction system of claim 1, wherein said computer system is configured for receiving supervisor input, to determine supervisor depiction data based on said supervisor input and transmitting said supervisor depiction data to said display unit.

35. The depiction system of claim 34, wherein said computer is configured for acquiring said supervisor input from a training database, via a digital user interface or by oral supervisor input.

36. The depiction system of claim 34, wherein said computer is configured for acquiring said supervisor input in the form of supervisor input representing selected positions and movements of the training tool.

37. The depiction system of claim 1, wherein said computer is programmed to receive instructions comprising classification data for selecting several 3D data sets and based on this instruction to acquiring selected 3D data sets and process the acquired 3D data sets to determine the resulting 3D data which is applied to determine the 3D surface contour of the surface section of the minimally invasive surgery cavity.

38. The depiction system of claim 1, wherein the determining of said real time spatial position data comprises determining a distance from the surgical tool to a critical structure of the surface section.

* * * * *